US012692232B2

(12) United States Patent
Cao et al.

(10) Patent No.: US 12,692,232 B2
(45) Date of Patent: Jul. 28, 2026

(54) INDOLE CARBOXAMIDE COMPOUND, PREPARATION THEREFOR AND USE THEREOF

(71) Applicant: NANJING RUISHUNING MEDICAL TECHNOLOGY CO., LTD., Nanjing City (CN)

(72) Inventors: Wei Cao, Yangling (CN); Dianchao Dong, Yangling (CN); Lei Zhou, Yangling (CN)

(73) Assignee: NANJING RUISHUNING MEDICAL TECHNOLOGY CO., LTD., Nanjing City (CN)

( * ) Notice: Subject to any disclaimer, the term of this patent is extended or adjusted under 35 U.S.C. 154(b) by 363 days.

(21) Appl. No.: 18/526,339

(22) Filed: Dec. 1, 2023

(65) Prior Publication Data

US 2024/0116869 A1 Apr. 11, 2024

Related U.S. Application Data

(63) Continuation of application No. PCT/CN2022/103268, filed on Jul. 1, 2022.

(30) Foreign Application Priority Data

Jul. 5, 2021 (CN) ......................... 202110757408.3

(51) Int. Cl.

| | |
|---|---|
| ***C07D 209/24*** | (2006.01) |
| ***A61P 9/00*** | (2006.01) |
| ***A61P 11/00*** | (2006.01) |
| ***A61P 13/12*** | (2006.01) |
| ***A61P 35/00*** | (2006.01) |

(52) U.S. Cl.

CPC .............. *C07D 209/24* (2013.01); *A61P 9/00* (2018.01); *A61P 11/00* (2018.01); *A61P 13/12* (2018.01); *A61P 35/00* (2018.01)

(58) Field of Classification Search

CPC .................................................... C07D 209/24
USPC .......................................................... 514/415
See application file for complete search history.

(56) References Cited

U.S. PATENT DOCUMENTS

2004/0235820 A1 11/2004 Tepe

FOREIGN PATENT DOCUMENTS

| | | |
|---|---|---|
| CN | 105820104 A | 8/2016 |
| CN | 109602745 A | 4/2019 |
| CN | 110483367 A | 11/2019 |

OTHER PUBLICATIONS

First Office Action issued in Chinese Application No. 202110757408.3; mailed Jun. 14, 2023; 7 pgs.

*Primary Examiner* — Kahsay Habte
(74) *Attorney, Agent, or Firm* — HAUPTMAN HAM, LLP

(57) ABSTRACT

The present invention relates to an indole carboxamide compound, preparation therefor and use thereof. The indole carboxamide is represented by the following general formula (I). The compound of the present invention is more stable and active and can be used for prophylaxis or treatment of nephropathy, sepsis, arthritis, pulmonary hypertension or tumor.

(I)

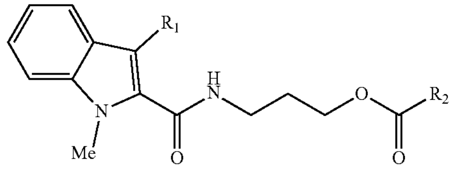

12 Claims, 2 Drawing Sheets

INDOLE CARBOXAMIDE COMPOUND, PREPARATION THEREFOR AND USE THEREOF

RELATED APPLICATIONS

The present application is a Continuation of International Application Number PCT/CN2022/103268 filed Jul. 1, 2022, and claims priority to Chinese Application Number 202110757408.3 filed Jul. 5, 2021, the disclosures of which is hereby incorporated by reference herein in their entireties.

TECHNICAL FIELD

The present invention belongs to the field of pharmaceutical technology and relates to an indole carboxamide compound, preparation therefor and use thereof.

BACKGROUND

Classical transient receptor potential canonical channels (TRPCs) are cation channels with non-selective ($Ca^{2+}$, $K^+$, $Na^+$) and permeable properties. They are widely expressed in many tissues, including lung, heart, brain, placenta, adrenal glands, retinal endothelium, testis, and kidney, and play key roles in many physiological and pathological processes of human beings, and participate in a variety of pathogenic mechanisms.

TRPC6 is a member of the classical transient receptor potential cation channel family, which consists of 931 amino acids and has a six-transmembrane structure. Current researches show that TRPC6 is widely distributed in various tissues of mammals, including brain, heart, kidney, lungs and many other important organs, and it plays an important role in many physiological processes, such as vascular smooth muscle contraction, podocyte signal transduction, central nervous system development and pain regulation, etc. TRPC6 proteins, as the molecular basis of $Ca^{2+}$ channel in cell membrane, are mainly involved in mediating receptor-operated calcium entry (ROCE). Its aberrant expression or gene mutation can cause alterations in intracellular $Ca^{2+}$ signaling pathway, which involves in many diseases.

In the cardiovascular system, TRPC6, as a positive regulator of calcineurin (NFAT) signal transduction, plays a regulatory role in cardiac function by mediating the activation of nuclear factor of activated T cells (NFAT) through mediating ROCE, which is closely related to pathogenesis of myocardial hypertrophy, myocardial ischemia/reperfusion injury, cardiac arrhythmia, and myocardial infarction. TRPC6 plays an important role in the development of cardiac hypertrophy. TRPC6 is also associated with stretch-induced arrhythmia. The regulation of TRPC6 in the cardiovascular system also includes the regulation of blood pressure. Vasoconstrictor neurotransmitters and some hormones, such as norepinephrine, angiotensin II, and vasopressin, etc., are able to activate TRPC6 channels and increase the rate of $Ca^{2+}$ transmembrane transport, which increases vascular tone and also promotes the proliferation of vascular smooth muscle cells, and this TRPC6-channel-mediated $Ca^{2+}$ dysregulation is thought to be one of the mechanisms for the development of essential hypertension. TRPC6 is also involved in regulation during the development of vascular-related diseases. TRPC6 exists in pulmonary artery smooth muscle, and hypoxia induces an elevation of its expression, which increases ROCE. The increase of intracellular calcium concentration makes pulmonary vascular smooth muscle cells proliferate, pulmonary artery wall thicken, lumen narrow, and finally form hypoxic pulmonary hypertension. TRPC6 expression is significantly increased in human and mouse atherosclerotic plaques. After the Trpc6 gene is knocked out, the ultrasound results of carotid artery in mice show that the vascular dysfunction caused by atherosclerosis, such as stenosis of vascular inner diameter, thickening of vascular wall and increase of blood flow resistance index, is significantly improved, the plaque area is significantly reduced, and the plaque stability is significantly increased, so that the TRPC6 is also a potential new target for atherosclerosis treatment.

TRPC6 can accelerate the progress of several acquired glomerular diseases, such as glomerulosclerosis associated with autoimmune glomerulonephritis, primary and secondary focal segmental glomerulosclerosis (FSGS), etc. Over activation of TRPC6 channels and mutation of TRPC6 gene can cause glomerular damage. TRPC6 is one of the podocyte proteins in the slit diaphragm, which mainly plays a role by mediating calcium ions entry. In diabetic nephropathy, reactive oxygen species and angiotensin (Ang) can lead to a dramatic increase in TRPC6-mediated $Ca^{2+}$ entry, which are the two main factors causing podocyte hypertrophy and death, and TRPC6 plays an important role in the regulation of diabetic nephropathy. The klotho proteins are known to have an inhibitory effect on renal fibrosis. Research has found that soluble klotho can significantly reduce obstructive-induced renal fibrosis in wild-type mice, but not in TRPC6 knockout mice, indicating that inhibition of klotho and TRPC6 may have an inhibitory effect on obstructive induced renal fibrosis through the same pathway. Therefore, TRPC6 is also a drug target for the treatment of renal fibrosis. TRPC6 gene knockout can alleviate interstitial fibrosis induced by unilateral ureteral obstruction (UUO) in mice. Therefore, inhibiting TRPC6 has become a promising new treatment strategy for chronic obstructive nephropathy and chronic renal failure.

TRPC6 is also closely related to the development of inflammation. The deletion of TRPC6 gene can inhibit the Toll-like receptor 4-related signaling pathway by regulating calmodulin, which in turn inhibits the nuclear factor kappa-B (NF-κB) and mitogen-activated protein kinase (MAPK) signaling pathways, attenuates endotoxin-caused inflammatory pathological injury of cardiac tissues, and ameliorates cardiac dysfunction, thus improving the survival rate of animals with endotoxemia. In the neuroinflammation model induced by 1-methyl-4-phenyl-1,2,3,6-tetrahydropyrrolidine (MPTP) in mice, it has found that the expression of TRPC6 is up-regulated, and TRPC6 gene knockout could increase the level of cryαB protein in microglia and reduce the expression of inflammatory factors, thus reducing the damage of dopaminergic neurons caused by inflammation. In addition, joint destruction due to inflammatory synovitis is a typical pathological process in rheumatoid arthritis, and IL-1β can participate in this process by inducing the proliferation of fibroblast-like synoviocytes; the mRNA expression level of TRPC6 in synovial tissues of patients with rheumatoid arthritis was markedly increased in relation to those of patients with osteoarthritis, whereas the silencing of TRPC6 markedly suppressed the IL-1β-induced proliferation of fibroblast-like synoviocytes in rheumatoid arthritis. Therefore, TRPC6 may play an important role in the disease development of rheumatoid arthritis. In addition, the protein expression of TRPC6 in lung tissues of an asthma model stimulated by ovalbumin sensitization is also significantly increased compared with that of the normal group, suggesting that TRPC6 may be associated with airway inflammation in asthmatic lung tissues, and thus be involved in the pathogenesis of asthma.

In addition, the proliferation of tumor cells and the synthesis of proteins for mitosis depend on the increase of intracellular calcium concentration. When TRPC6 functions abnormally, a large amount of $Ca^{2+}$ enters into the cells through ROCE, initiating the cell cycle and promoting cell proliferation, and TRPC6 is highly expressed in a variety of human cancer cells, including glioma, esophageal carcinoma, renal carcinoma, pancreatic carcinoma, breast carcinoma, lung carcinoma, liver carcinoma, colorectal cancer, etc. Knockdown of TRPC6 gene can inhibit the growth and invasion of glioblastoma through the NFAT pathway and induces cell cycle to stop at G2/M phase. In human oral squamous cell carcinoma (OSCC), TRPC6 protein and mRNA levels were significantly higher than those in normal subjects, and TRPC6 blockade was able to inhibit the elevation of calcium concentration and the activation of Cdc2 kinase in esophageal carcinoma cells, which resulted in tumor cell-cycle to stop at G2 phase. The content of TRPC6 in human renal cancer cells was much higher than that in normal subjects. Hepatocyte growth factor (HGF) was able to up-regulate the expression of TRPC6 and induced the proliferation of human renal cancer cells, and knockdown of TRPC6 was able to significantly inhibit the proliferation of renal cancer cells induced by HGF. TRPC6 is expressed in the low metastatic breast cancer cell line MCF-7 and the high metastatic breast cancer cell line MDA-MB-231, and can form an intracellular heterotrimeric complex with TRPC3 to regulate breast cancer growth.

These studies above illustrate that upregulation of TRPC6 function is a pathological mechanism leading to numerous diseases; TRPC6 inhibitors have become therapeutic targets for many of these related diseases. Therefore, the research on small molecule inhibitors of TRPC6 has become a research hotspot in related fields.

According to reports, compounds that can significantly inhibit TRPC6 channel-mediated $Ca^{2+}$ entry include SKF96365, SAR7334 and Guanidine derivatives. However, due to the large number of members of the TRPC protein family and the high degree of amino acid sequence similarity, different members can polymerize to form heterotetramers, resulting in a large diversity of protein channels in the family, and few specific inhibitors targeting TRPC6 have been reported. SAR7334 only inhibits TRPC3/7 to varying degrees, and SKF96365 inhibited other TRPC family proteins to varying degrees. Therefore, the development of new specific inhibitors that can target TRPC6 is important for the treatment of the disease.

CN2019107285315 discloses use of an indole analogue in the preparation of a medicament, but the compounds have the prominent drawbacks of weak activity and poor stability, resulting in a limited application of the compounds as medicaments. Therefore, there is still a demand for indole-carboxamide compounds with better activity and stability.

SUMMARY OF THE INVENTION

Aiming at the disadvantages of poor stability and weak activity of the indole compounds disclosed in CN2019107285315, the purpose of the present invention is to provide a new indole carboxamide compound and preparation method therefor and use thereof. The indole carboxamide compound of the present invention has TRPC6 inhibitory effect, enhanced stability and increased activity, which better meets the requirements for clinical use of the compounds.

In order to achieve the above objects, a first aspect of the present invention is to provide an indole carboxamide compound represented by the following general formula (I), isomers thereof, pharmaceutically acceptable salts thereof, esters thereof or prodrugs thereof:

(I)

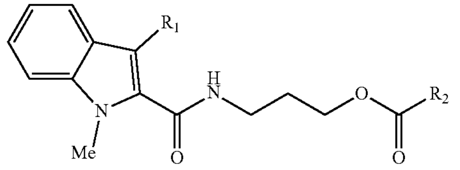

wherein:

$R_1$ is selected from the group consisting of hydrogen atom, hydroxyl, aldehyde group, halogen, guanidino, $C_{1-6}$ alkyl, $C_{2-6}$ alkenyl, $C_{2-6}$ alkynyl, 6- to 14-membered aryl, $C_{3-10}$ cycloalkyl, 3- to 10-membered heterocycloalkyl, 5- to 6-membered heteroaryl, $C_{1-6}$ alkyloxy, 6- to 14-membered aryloxy, $-OCH_2$-6- to 14-membered aryl, $-CF_3$, $-OCHF_2$, $-OCF_3$, $-CN$, nitro group, carboxyl, $-C(O)O-C_{1-6}$ alkyl, $-CH(OH)-C_{1-6}$ alkyl, $-CH(O-C_{1-6}$ alkyl)-$C_{1-6}$ alkyl, $-C(O)N-C_{1-6}$ alkyl, amino group, $-NHC(O)-C_{1-6}$ alkyl, $-NHC(O)$-6~14-membered aryl, $-N-(C_{1-6}$ alkyl)$_2$, $-NHS_2$-6~14-membered aryl, $-S-C_{1-6}$ alkyl, $-SO-C_{1-6}$ alkyl, $-SO_2-C_{1-6}$ alkyl, $-SO_2$6~14-membered aryl or a heterocyclic ring containing 1~4 heteroatoms selected from N, O and S, or two adjacent substituent groups together with the atom to which they are attached may form a 3~10-membered ring structure; the $C_{1-6}$ alkyl, the 6- to 14-membered aryl, the $C_{3-10}$ cycloalkyl, the 3- to 10-membered heterocycloalkyl and the 5- to 6-membered heteroaryl are optionally substituted with 1 to 5 substituents selected from a group consisting of hydroxyl, $C_{1-6}$ alkyl, nitro group, sulfonic group, halogen, cyano, trifluoromethyl, difluoromethoxy, and trifluoromethoxy; and the 3- to 10-membered heterocycloalkyl and the 5- to 6-membered heteroaryl optionally contain 1 to 6 heteroatoms selected from N, O and S;

$R_2$ is selected from the group consisting of hydrogen atom, $C_{1-10}$ alkyl, 6- to 14-membered aryl, $C_{3-10}$ cycloalkyl, 5- to 10-membered heterocycloalkyl, 5- to 6-membered heteroaryl, $-C(O)-C_{3-10}$ alkyl, amino group, substituted amino group, amidino group, guanidino, or metal ion; wherein the $C_{1-10}$ alkyl, the 6- to 14-membered aryl, the $C_{3-10}$ cycloalkyl, the 5- to 10-membered heterocycloalkyl or the 5- to 6-membered heteroaryl are optionally substituted with 1 to 2 substituents selected from the group consisting of hydroxyl, nitro group, halogen, cyano, trifluoromethyl, $C_{1-6}$ alkoxy, 6- to 8-membered aryl, trifluoromethoxy, difluoromethoxy and $C_{1-6}$ alkyl; and the 5- to 10-membered heterocycloalkyl and the 5- to 6-membered heteroaryl optionally contain 1 to 6 heteroatoms selected from N, O and S.

$R_1$ is a substituent on No. 3 carbon atom of the indole mother nucleus; $R_2$ is a substituent on the acyl group.

Preferably, in the general formula (I):

$R_1$ is selected from the group consisting of hydrogen atom, hydroxyl, aldehyde group, halogen, 6- to 14-membered aryl group, $C_{3-10}$ cycloalkyl, —CN, amino group, nitro group, —NHC(O)—6- to 14-membered aryl, —N—$(C_{1-6}\ alkyl)_2$ or —$NHSO_2$-6- to 14-membered aryl, or two adjacent substituent groups together with the atom to which they are attached form a 5- to 6-membered ring structure;

$R_2$ is selected from the group consisting of hydrogen atom, $C_{1-3}$ alkyl group and phenyl.

Further preferably, in general formula (I):

$R_1$ is selected from the group consisting of hydrogen atom, aldehyde group, amino group, phenyl or benzamido, or two adjacent substituent groups together with the atom to which they are attached form a benzene ring;

$R_2$ is selected from the group consisting of hydrogen atom, $C_{1-3}$ alkyl group and phenyl.

Further preferably, the indole carboxamide compound represented by general formula (I), isomers thereof, pharmaceutically acceptable salts thereof, esters thereof or prodrugs thereof is selected from the following compounds, isomers thereof, pharmaceutically acceptable salts thereof, esters thereof or prodrugs thereof:

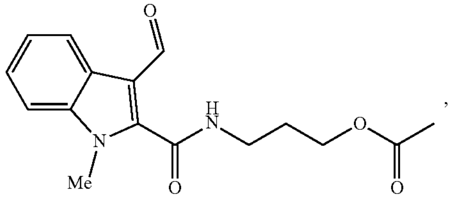
,

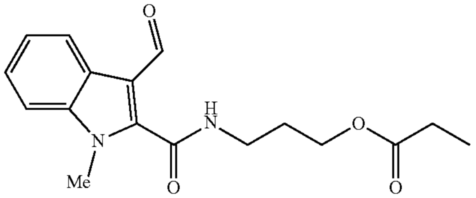
,

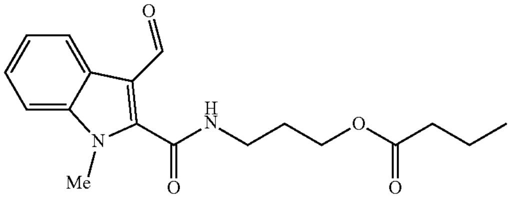
,

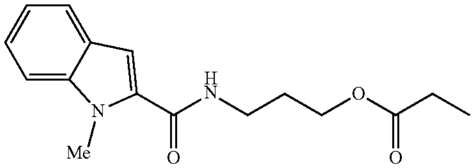
,

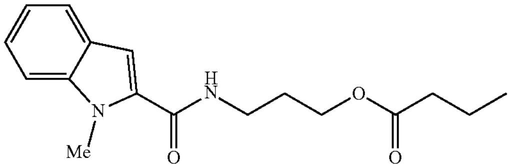
,

-continued

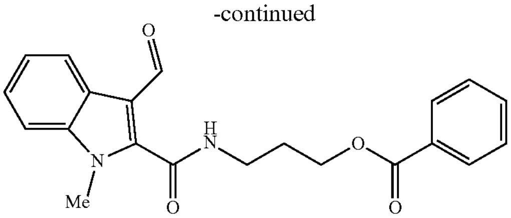
,

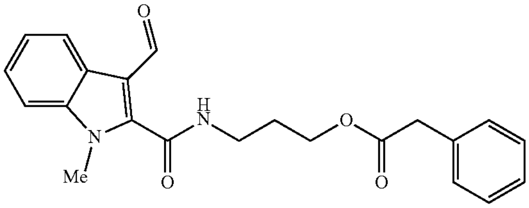
or

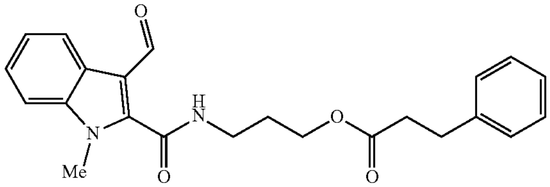
;

Further preferably, the indole carboxamide compound represented by the general formula (I), isomers thereof, pharmaceutically acceptable salts thereof, esters thereof or prodrugs thereof is one of the following compounds, isomers thereof, pharmaceutically acceptable salts thereof, esters thereof or prodrugs thereof:

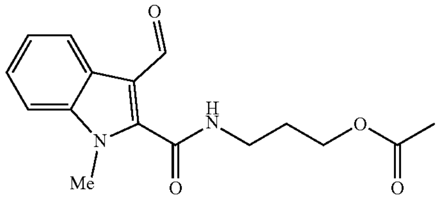
or

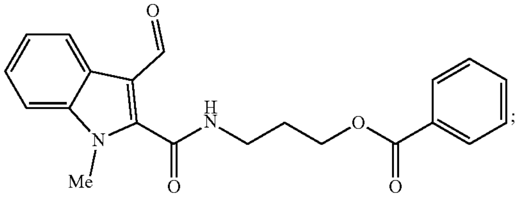
;

Even further preferably, the indole carboxamide compound represented by the general formula (I), isomers thereof, pharmaceutically acceptable salts thereof, esters thereof, solvates thereof or prodrugs thereof is selected from the following compounds, isomers thereof, pharmaceutically acceptable salts thereof, esters thereof or prodrugs thereof:

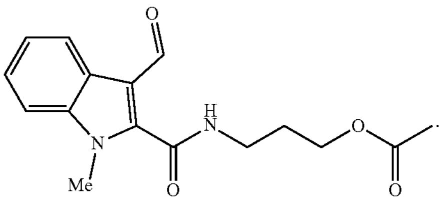
.

"Halogen" as used in the present invention means fluorine, chlorine, bromine or iodine as a substituent. When a halogen atom is used as a substituent, the number of substituents is more than one, including one, two, or three, and the like.

"$C_{1-6}$ alkyl" as used in the present invention means a linear or branched alkyl group derived by removing a hydrogen atom from an alkane containing 1 to 6 carbon atoms. The alkyl group may optionally be substituted with 1 to 5 appropriate substituents, such as hydroxyl, nitro group, sulfonic acid group, halogen, cyano, trifluoromethyl, trifluoromethoxy or difluoromethoxy.

"$C_{2-6}$ alkenyl" as used in the present invention means a linear or branched alkenyl or cyclic alkenyl containing a carbon-carbon double bond and 2 to 6 carbon atoms. The alkenyl may optionally be substituted with 1 to 5 appropriate substituents, such as hydroxyl, nitro group, sulfonic acid group, halogen, cyano, trifluoromethyl, trifluoromethoxy or difluoromethoxy.

"$C_{2-6}$ alkynyl" as used in the present invention means a linear or branched alkynyl or cyclic alkynyl containing a carbon-carbon triple bond and 2 to 6 carbon atoms. The alkynyl group may optionally be substituted with 1 to 5 appropriate substituents, such as hydroxyl, nitro group, sulfonic acid group, halogen, cyano, trifluoromethyl, trifluoromethoxy or difluoromethoxy.

"$C_{3-10}$ cycloalkyl" as used in the present invention is a fully hydrogenated non-aromatic ring consisting of a mono-, bicyclic or tricyclic ring containing 3 to 10 carbon atoms. Thus, the cycloalkyl may be a monocyclic ring typically containing 3 to 7 ring atoms. Examples include, but are not limited to, cyclopropyl, cyclobutyl, cyclopentyl, and cyclohexyl. Alternatively, 2 or 3 rings may be fused together, such as bicyclodecyl and decalinyl. Moreover, "cycloalkyl" includes bridged bicycloalkyl systems, such as, but not limited to, bicyclo[2.2.1]heptane and bicyclo[1.1.1]pentane. The cycloalkyl may optionally be substituted with 1 to 5 appropriate substituents, such as hydroxyl, nitro group, sulfonic acid group, halogen, cyano, trifluoromethyl, trifluoromethoxy or difluoromethoxy.

"$C_{1-6}$ alkoxy" as used in the present invention means a group derived from a compound formed by connecting "$C_{1-6}$ alkyl" and other parts by —O—.

"6-14-membered aryl" of the present invention means a cyclic aromatic group with 6-14 carbon atoms as ring atoms, including 6-8-membered monocyclic aryl and 8-14-membered fused cyclic aryl. The 6-8 monocyclic aryl means completely unsaturated aryl, and 8-14 fused cyclic aryl means a cyclic group formed by two or more cyclic structures sharing two adjacent carbon atoms with each other, with at least one ring being a completely unsaturated aromatic ring. The aryl may optionally be substituted with 1 to 5 appropriate substituents, such as hydroxyl, nitro group, sulfonic acid group, halogen, cyano, trifluoromethyl, trifluoromethoxy or difluoromethoxy.

"3 to 10-membered heterocycloalkyl" as used in the present invention means a stable 3 to 10-membered monocyclic ring, which is a monovalent saturated group comprising 1 to 3 rings containing 1, 2, 3 or 4 heteroatoms (N, O or S) and 3 to 9 carbon atoms, wherein the nitrogen and sulphur heteroatoms can be selectively oxidized and the nitrogen heteroatoms selectively quaternized, and is preferably a 5-membered and 6-membered heterocycloalkyl. Examples of heterocycloalkyl include, but are not limited to: optionally substituted piperidinyl, piperazinyl, homopiperazinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinolinyl, isoquinolinyl, benzoimidazolyl, thiadiazolidinyl, benzothiazolidinyl, benzooxazolidinyl, dihydrofuranyl tetrahydrofuranyl, dihydropyranyl, tetrahydropyranyl, thiomorpholinyl, thiomorpholino sulfoxide group, thiomorpholino sulfone group, dihydroquinolinyl, tetrahydroquinolinyl, tetrahydroisoquinolinyl, etc.

"5 to 6-membered heteroaryl" as used in the present invention means an aromatic ring structure containing 5 to 6 ring atoms, wherein at least one of the ring atoms is a heteroatom (N, O or S) and the remaining ring atoms are independently selected from the group consisting of carbon, oxygen, nitrogen and sulfur. Examples of heteroaryl substituents include 6-membered ring substituents (such as pyridinyl, pyrazinyl, pyrimidinyl and pyridazinyl) and 5-membered ring substituents (such as triazolyl, imidazolyl, furanyl, thienyl, pyrazolyl, oxazolyl, isoxazolyl, thiazolyl, 1,2,3-, 1,2,4-, 1,2,5-, or 1,3,4-oxadiazolyl and isothiazolyl). In a moiety having a heteroaryl substituent, the ring atom to which the heteroaryl substituent is bonded may be one of the heteroatoms, or it may be a ring carbon atom. Similarly, if the heteroaryl substituent is substituted by a group or substituent, the group or substituent may be bonded to one of the heteroatoms, or it may be bonded to a ring carbon atom. "Heteroaryl" also includes pyridinyl N-oxide and groups containing a pyridinyl N-oxide ring.

"Salt" as used in the present invention means a pharmaceutically acceptable salt, and "pharmaceutically acceptable salt" means a salt prepared by combining a compound represented by the general formula (I) with an acid or a base, wherein the anion of the acid or the cation of the base is generally considered to be suitable for use in the human body. The salt is usually prepared by reacting a suitable inorganic or organic acid with a free base, which includes salts derived from inorganic acids (e.g., hydrochloric acid, hydrobromic acid, hydrofluoric acid, boronic acid, fluoboric acid, phosphoric acid, metaphosphoric acid, nitric acid, carbonic acid, sulfonic acid and sulfuric acid) and organic acids (e.g., acetic acid, benzenesulfonic acid, benzoic acid, citric acid, ethylsulfonic acid, fumaric acid, gluconic acid, glycolic acid, 2-hydroxyethanesulfonic acid, lactic acid, lactobionic acid, maleic acid, malic acid, methyl sulfonic acid, trifluoromethanesulfonic acid, butanedioic acid, toluene sulfoni c acid, tartaric acid and trifluoroacetic acid). Suitable organic acids typically include organic acids, for example, aliphatic acids, cycloaliphatic acids, aromatic acids, arylaliphatic acids, heterocyclic acids, carboxylic acids and sulfonic acids.

Specific examples of suitable organic acid salts include acetates, trifluoroacetates, formates, propionates, succinates, glycolates, gluconates, digluconates, lactates, malates, tartrates, citrates, ascorbates, glucuronates, maleates, fumarates, pyruvates, aspartates, glutamates, benzoates, o-aminobenzoates, stearates, salicylates, p-hydroxybenzoates, phenylacetates, mandelates, embonates(pamoates), methanesulfonates, ethanesulfonates, benzenesulfonates, pantothenates, toluenesulfonates, 2-hydroxyethanesulfonates, p-aminobenzenesulfonate, cyclohexylamino sulfonates, alginates, beta-hydroxybutyrates, mucates, galacturonates, adipates, alginates, butyrates, camphorates, camphor sulfonates, cyclopentyl propionates, dodecyl sulfates, glucoheptonates, glycerophosphates, heptanoates, caproates, nicotinates, 2-naphthalenesulfonates, oxalates, pectates, 3-phenylpropionates, picrates, neopentanoates, thiocyanates and undecanoates.

When the compounds of the present invention have acidic groups, suitable pharmaceutically acceptable salts thereof may include alkali metal salts (e.g., sodium or potassium salts), alkaline earth metal salts (e.g., calcium or magnesium salts), and salts formed with suitable organic ligands (e.g., quaternary ammonium salts). There are also other forms of alkali salts, including aluminum salts, arginine salts, benzylpenicillin (benzathine) salts, choline salts, diethylamine salts, diethanolamine salts, glycine salts, lysine salts, meglumine salts, cholamine salts, tromethamine salts and zinc salts. Organic salts may be formed by secondary, tertiary, or quaternary amines (e.g., tromethamine, diethylamine, N,N'-dibenzylethylenediamine, chloroprocaine, choline, diethanolamine, ethylenediamine, N-methylglucosamine and procaine).

"Ester" as used in the present invention means an ester formed by a hydroxyl group present in the compounds provided herein with a suitable acid, such as a carboxylic acid or an oxygen-containing inorganic acid. Suitable ester groups include, but are not limited to, formates, acetates, propionates, butyrates, benzoates, acrylates, ethylsuccinates, stearates or palmitates.

"Isomer" as used in the present invention includes cis and trans isomers, optical isomers (e.g., R and S enantiomers), diastereomers, geometrical isomers, rotamers, conformational isomers and tautomers of compounds, which includes compounds displaying more than one isomerization phenomenon and mixtures thereof (e.g., racemic isomers and diastereomers). At the same time, it also includes the form of compound salts, such as D-lactate or L-lysine; or in racemic form, such as DL-tartrate or DL-arginine.

A second aspect of the present invention is to provide a method for preparing the indole carboxamide compound represented by the above general formula (I), isomers thereof, pharmaceutically acceptable salts thereof, esters thereof or prodrugs thereof. The method can be any one of the following two general methods, and the specific synthesis method varies according to the reaction materials.

method 1

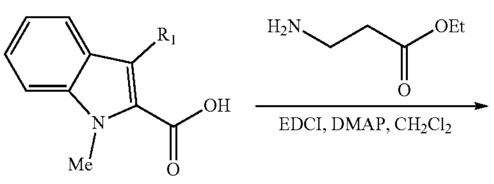

A

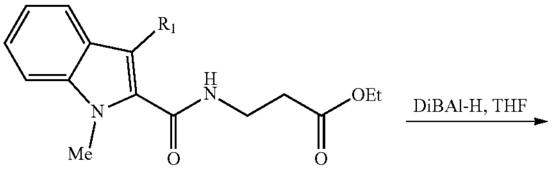

B

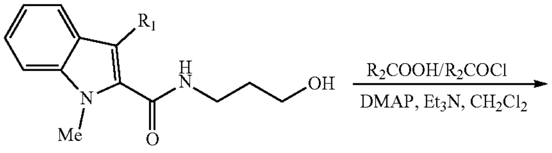

C

-continued

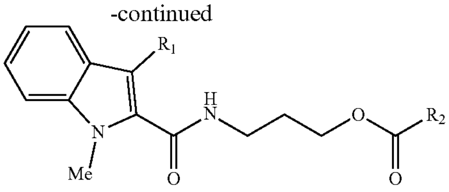

D wherein, $R_1$ and $R_2$ are defined as above;

Compound A is dissolved in anhydrous dichloromethane ($CH_2Cl_2$), 1-(3-dimethylaminopropyl)-3-ethylcarbodiimide hydrochloride (EDCI) is dissolved in anhydrous $CH_2Cl_2$, and β-alanine ethyl ester and 4-dimethylaminopyridine (DMAP) are dissolved in anhydrous $CH_2Cl_2$, and then the three solutions are mixed and reacted under stirring in an ice bath, and then reacted at room temperature, and the reaction is monitored by TLC until it is complete; then the reaction is quenched by adding saturated $NH_4Cl$ solution drop by drop; thus obtained mixture is extracted with $CH_2Cl_2$, the lower layer solution is collected, dried with anhydrous $Na_2SO_4$, filtered, concentrated, and purified by column chromatography to give product B;

the product B obtained above is dissolved in anhydrous tetrahydrofuran (THF) under stirring, and diisobutylaluminum hydride (DIBAl-H) at a concentration of 1 mol/L is added drop by drop thereto, the reaction is carried out at 0° C. and monitored by TLC until it is complete; methanol (MeOH) is then added drop by drop to quench the reaction, followed by adding a small amount of methyl tertiary-butyl ether (MTBE) to dilute the reaction system, and saturated sodium potassium tartrate solution is added to further quench the reaction, and stirring is continued until the reaction system is clarified; thus obtained mixture is extracted with ethyl acetate (EtOAc), the organic phases are combined, washed with a small amount of saturated brine, and then dried with anhydrous $Na_2SO_4$, concentrated after a few moments of standing, and then purified by column chromatography to give product C;

the product C obtained above is dissolved in anhydrous $CH_2Cl_2$ under stirring; followed by successively adding triethylamine and DMAP at room temperature, and finally compound $R_2COOH$ or its anhydride, or its acyl chloride $R_2COCl$ is added drop by drop to initiate reaction; the reaction is monitored by TLC until it is complete; saturated $NH_4Cl$ solution is added drop by drop to quench the reaction, thus obtained mixture is extracted with EtOAc, the organic phases are combined, washed with a small amount of saturated brine, dried with anhydrous $Na_2SO_4$, filtered, concentrated and purified by column chromatography to give product D.

Method 2

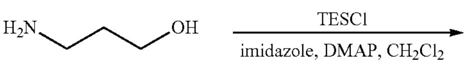

-continued

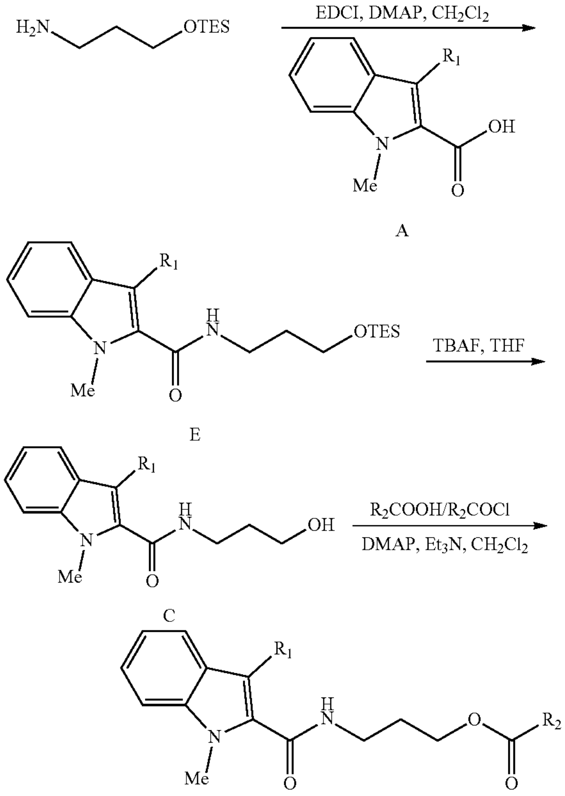

A
E
C
D wherein, $R_1$ and $R_2$ are defined as above;

3-aminopropanol is dissolved in anhydrous $CH_2Cl_2$, followed by adding imidazole and 4-dimethylaminopyridine (DMAP), and finally triethylchlorosilane (TESCl) is added thereto under stirring at room temperature, and the reaction is monitored by TLC until it is complete; saturated $NH_4Cl$ solution is added drop by drop to quench the reaction, and then thus obtained mixture is extracted with ethyl acetate (EtOAc), the organic phases are combined, washed with a small amount of saturated brine, and then dried with anhydrous $Na_2SO_4$, filtered, concentrated, and purified by column chromatography to give 3-triethylsilyloxy-1-propanamine;

the compound A is dissolved in anhydrous $CH_2Cl_2$, 1-(3-dimethylaminopropyl)-3-ethylcarbodiimide hydrochloride (EDCI) is dissolved in anhydrous $CH_2Cl_2$, 3-triethylsilyloxy-1-propanamine and DMAP are dissolved in anhydrous $CH_2Cl_2$, and then the above three solutions are mixed, and thus obtained mixture is stirred in an ice bath and reacted at room temperature, and the reaction is monitored by TLC until it is complete; thus obtained mixture is extracted with $CH_2Cl_2$, and the lower layer solution is collected and dried overnight with anhydrous $Na_2SO_4$, then filtered and concentrated, and purified by column chromatography to give product E;

the compound E is dissolved in anhydrous tetrahydrofuran (THF), followed by adding a small amount of tetrabutylammonium fluoride (TBAF) under stirring at room temperature and the reaction is monitored by TLC until it is complete. The reaction is quenched by adding saturated $NH_4Cl$ solution drop by drop, thus obtained mixture is extracted with EtOAc, and the organic phases are combined, washed with a small amount of saturated brine, dried with anhydrous $Na_2SO_4$, filtered, concentrated, and purified by column chromatography to give product C;

the product C obtained above is dissolved in anhydrous $CH_2Cl_2$ under stirring, followed by successively adding triethylamine ($Et_3N$) and DMAP at room temperature, and finally compound $R_2COOH$ or its anhydride, or its acyl chloride $R_2COCl$ is added drop by drop to initiate reaction; the reaction is monitored by TLC until it is complete; saturated $NH_4Cl$ solution is added drop by drop to quench the reaction, thus obtained mixture is extracted with EtOAc, the organic phases are combined, washed with a small amount of saturated brine, dried with anhydrous $Na_2SO_4$, filtered, concentrated, and purified by column chromatography to give product D.

Those skilled in the art will understand that the specific synthesis methods of different compounds vary according to the raw materials.

A third aspect of the present invention is to provide use of the indole carboxamide compound represented by the general formula (I) of the present invention, isomers thereof, pharmaceutically acceptable salts thereof, esters thereof, prodrugs thereof in the manufacture of a medicament as a TRPC6 inhibitor.

Preferably, the present invention provides use of the indole carboxamide compound represented by the general formula (I) of the present invention, isomers thereof, pharmaceutically acceptable salts thereof, esters thereof, prodrugs thereof in the manufacture of an inhibitor for inhibiting TRPC6 channel-mediated $Ca^{2+}$ entry.

Preferably, the present invention provides use of the indole carboxamide compound represented by the general formula (I) of the present invention, isomers thereof, pharmaceutically acceptable salts thereof, esters thereof, prodrugs thereof in the manufacture of a medicament for prophylaxis or treatment of nephropathy, sepsis, arthritis, pulmonary hypertension or tumor.

Preferably, the nephropathy is a primary glomerular disease, including primary nephrotic syndrome, IgA nephropathy, acute glomerulonephritis, focal segmental glomerulosclerosis, renal fibrosis, idiopathic membranous nephropathy, and membranoproliferative glomerulonephritis; metabolic disease-associated renal damage, including diabetic nephropathy, hyperuricemic nephropathy and obesity-related glomerulopathy; chronic renal failure, including cardiovascular complications due to renal anemia and chronic renal failure; and infection-related renal damage including hepatitis B virus-related nephritis, and kidney injury due to infective endocarditis.

Preferably, the sepsis comprises sepsis and septic shock caused by a variety of different pathogenic bacteria, including, but not limited to: *Staphylococcus aureus* septicemia, septicemia caused by *Staphylococcus epidermidis, Enterococcal septicemia*, gram-negative *Bacillus* septicemia, anaerobic bacteria septicemia, fungal septicemia and septic shock.

Preferably, the pulmonary hypertension comprises, but is not limited to: pulmonary arterial hypertension, pulmonary hypertension due to left heart disease, pulmonary hypertension due to hypoxia and/or lung disease, chronic thromboembolic pulmonary hypertension, pulmonary hypertension due to multiple mechanisms and/or unknown mechanisms.

Preferably, the tumor comprises a malignant tumor; the malignant tumor comprises, but is not limited to: glioma, esophageal cancer, renal cancer, pancreatic cancer, breast cancer, lung cancer, liver cancer and colorectal cancer.

A fourth aspect of the present invention is to provide a pharmaceutical composition comprising the indole carboxamide compound represented by the general formula (I), isomers thereof, pharmaceutically acceptable salts thereof, esters thereof or prodrugs thereof, and a pharmaceutically acceptable excipient.

Preferably, the dosage forms of the pharmaceutical composition may be tablets, pills, capsules, granules, dispersions, syrups, films, ointments, suppositories, suspensions, injections, liposomes, gels, aerosols (powders) or sprays.

The pharmaceutical composition may be formulated in any of the clinically or pharmaceutically acceptable dosage form known in the art and is intended for patients who need preventive or therapeutic treatment by oral administration, sublingual administration, parenteral administration, rectal administration, cutaneous administration or pulmonary administration. When used for oral administration, it can be made into tablets, pills, capsules, granules, dispersions, film agents, syrups and suspensions. When used for sublingual administration, it can be made into tablets, pills, granules, film agents and dispersions. When used for parenteral gastrointestinal administration, it can be made into injections, including injection solution, sterile powders for injection, concentrated solution for injection and liposome injections. When used for rectal administration, it can be made into a suppository. When used for cutaneous administration, it can be made into ointments, gels, film agents, etc. When used for pulmonary administration, it can be made into aerosols (powder aerosols), sprays, etc.

Compared with the compound disclosed in CN2019107285315, the indole carboxamide compound represented by the general formula (I) of the present invention, isomers thereof, pharmaceutically acceptable salts thereof, esters thereof, prodrugs thereof are obviously more stable, and in the process of preventing or treating diseases requiring long-term medication, such as nephropathy, sepsis, arthritis, pulmonary hypertension, or tumor, etc., the composition of the medicament does not change significantly, thus providing a stable and long-lasting therapeutic effect. More importantly, compared with the compound disclosed in CN2019107285315, the indole carboxamide compound represented by the general formula (I) of the present invention, isomers thereof, pharmaceutically acceptable salts thereof, esters thereof, prodrugs thereof have a stronger blocking effect on the calcium channel, and have higher activity in preventing or treating diseases such as nephropathy, sepsis, arthritis, pulmonary hypertension or tumors, and have remarkable effects.

BRIEF DESCRIPTION TO THE DRAWING

MODE OF CARRYING OUT THE INVENTION

Figure 1:
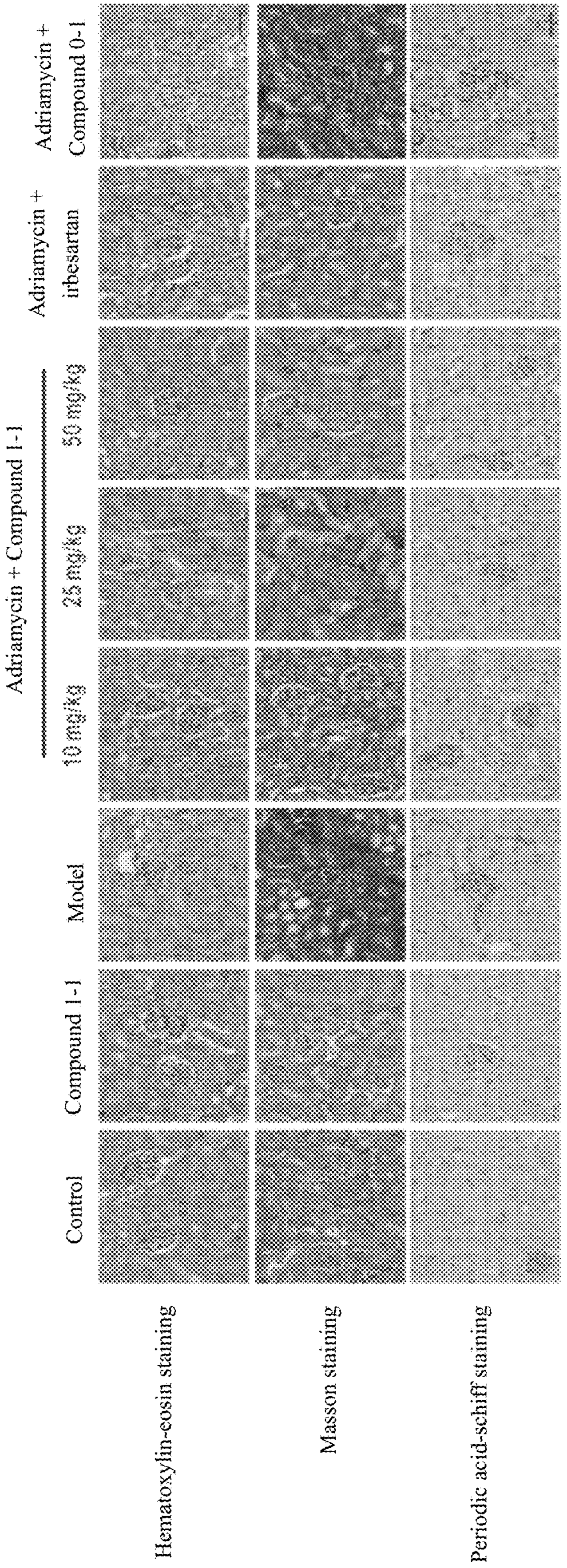
FIG. 1 shows FSGS-induced renal tissues after treatment with compound 1-1 of the present invention, which are stained with hematoxylin-eosin stain, periodic acid-schiff stain and Sirius red stain, respectively. Note: Compound 0-1 is 3-[(1-methyl-1H-indole-2-carbonyl)amino]propionic acid, which is the most active indole analogue disclosed in CN2019107285315.

The following examples further illustrate the present invention, but do not constitute any form of limitation to the present invention.

Example 1: Preparation of propyl 3-[(3-formyl-1-methyl-1H-indole-2-carbonyl)amino]acetate (Compound 1-1)

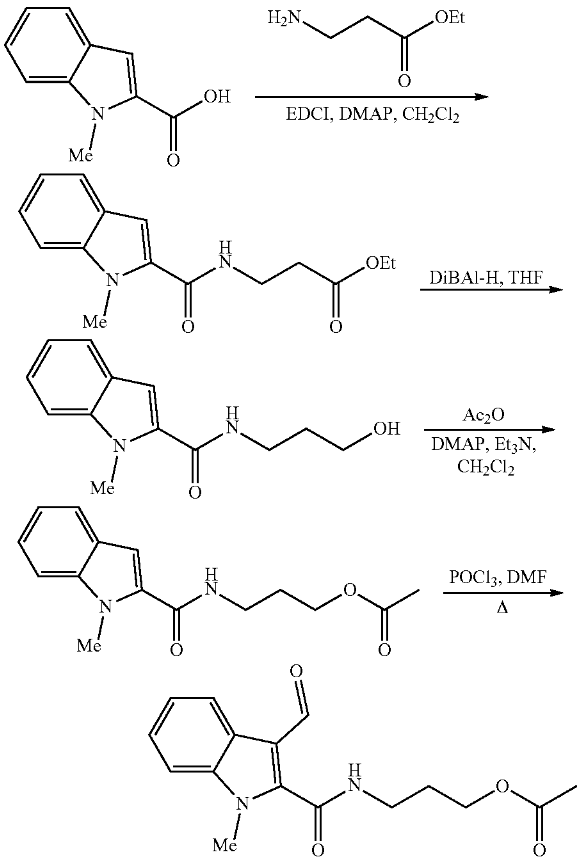

Step 1: Preparation of ethyl 3-[(1-methyl-1H-indole-2-carbonyl)amino]propanoate Under anhydrous conditions, compound 1-methyl-2-indolecarboxylic acid (490 mg, 2.8 mmol, 1 eq.) was dissolved in anhydrous $CH_2Cl_2$ (10 mL) at 0° C. under stirring, followed by adding solid DMAP (596.4 mg, 4.76 mmol, 1.7 eq.) in powder form and solid EDCI (609 mg, 3.08 mmol, 1.1 eq.), and finally β-alanine ethyl ester hydrochloride powder (488.6 mg, 3.08 mmol, 1.1 eq.) was added to initiated the reaction. The reaction was monitored by TLC (petroleum ether/ethyl acetate=2:1). After natural melting of the ice water bath, the reaction was allowed to continue at room temperature for approximately 12 hours until it was complete. Saturated ammonium chloride ($NH_4Cl$) solution was then added drop by drop to quench the reaction. Thus obtained mixture was extracted with ethyl acetate (EtOAc), and the organic phases were combined, washed with saturated brine, dried with anhydrous sodium sulfate ($Na_2SO_4$), and left to stand for a few moments, then evaporated and concentrated to give a crude product. The crude product was purified by column chromatography to give 700 mg (2.52 mmol) of ethyl 3-[(1-methyl-1H-indole-2-carbonyl)amino] propanoic acid derivatives with a yield of 89%.

Step 2: Reduction of the Terminal Ester Group of the Compound to a Hydroxyl Group Under anhydrous and oxygen-free conditions, the product obtained above (621.4 mg, 2 mmol, 1 eq.) was dissolved in anhydrous tetrahydrofuran (THF, 15 mL) at 0° C. under stirring. Diisobutylaluminium hydride (DIBAl-H, 8 mL) at a concentration of 1 mol/L was added drop by drop thereto and the reaction was carried out at 0° C. The reaction was monitored by TLC (petroleum ether/ethyl acetate=1:1). Then methanol (MeOH, 5 mL) was added drop by drop to quench the reaction, a small amount of methyl tertiary-butyl ether (MTBE) was added to dilute the reaction system, followed by adding saturated sodium potassium tartrate solution to further quench the reaction, and the stirring was continued until the reaction system was clarified. After clarification, the reaction system was extracted with EtOAc, the organic phases were combined, washed with a small amount of saturated brine, and then the organic phases were dried with anhydrous $Na_2SO_4$, left to stand for a few moments and then concentrated by rotary evaporation to give a crude product which was purified by column chromatography to give 236.4 mg (0.86 mmol) of product with a yield of 44%.

Step 3: Esterification of Hydroxyl Group at the End of the Carbon Chain

Under anhydrous conditions, a total of 222.2 mg (0.83 mmol, 1 eq.) of the product obtained above was dissolved in anhydrous $CH_2Cl_2$ (10 mL) at ambient temperature under stirring. Then triethylamine ($Et_3N$, 0.23 mL, 1.66 mmol, 2 eq.) and DMAP (10 mg, 0.08 mmol, 0.1 eq.) were added successively at room temperature, and finally the reaction was initiated by adding acetic anhydride ($Ac_2O$, 0.11 mL, 1.25 mmol, 1.5 eq.) drop by drop. The reaction was monitored by TLC (petroleum ether/ethyl acetate=1:1). The reaction was quenched by adding saturated $NH_4Cl$ solution drop by drop, then thus obtained mixture was extracted with EtOAc, the organic phases were combined, washed with a small amount of saturated brine, and then the organic phases were dried with anhydrous $Na_2SO_4$, left to stand for a few moments and then concentrated by rotary evaporation to obtain a crude product, which was purified by column chromatography to give 205.4 mg (0.75 mmol) of product with a yield of 90%.

Step 4: Introduction of Aldehyde Group on No. 3 Carbon Atom of Indole by Using Vilsmeier-Haack Reaction Firstly, under anhydrous and oxygen-free conditions at 0° C., N,N-dimethylformamide (DMF, 3 mL) and $POCl_3$ (0.12 mL) were mixed under stirring at 0° C. for 30 min, and then the ice-water bath was withdrawn, and the mixing and stirring continued for another 30 min to give disubstituted formamide-phosphorochloride required for the reaction. Under anhydrous and oxygen-free conditions, DMF (3 mL) was added drop by drop to dissolve 198.5 mg (0.74 mmol, 1 eq.) of the product obtained above at 0° C. The dissolved feedstock was then added to the prepared disubstituted formamide-phosphorochloride drop by drop, and the process was repeated twice with DMF (1.5 mL). When the addition was complete, the ice water bath was removed and the temperature gradually increased to 50° C. to continue the reaction.

The reaction was monitored by TLC and the reaction was complete after about 5 hours. A small amount of MTBE was then added to dilute the reaction system and the reaction was quenched by adding a small amount of distilled water with continuous stirring for about 30 minutes. The reaction system was extracted with EtOAc, the organic phases were combined, washed with a small amount of saturated brine, and then the organic phases were dried with anhydrous $Na_2SO_4$, left to stand for a few moments and then concentrated by rotary evaporation to give a crude product which was purified by column chromatography to give 89.6 mg (0.30 mmol) of product with a yield of 41%. The compound was confirmed by IR, $^1H$ NMR, ESI-MS, $^{13}C$ NMR and the structure was correct, i.e., propyl 3-[(1-methyl-1H-indole-2-carbonyl)amino]acetate.

Molecular formula: $C_{16}H_{18}N_2O_4$; Molecular weight: 302, ESI-MS m/z: 325.11588 $[M+Na]^+$; $^1H$ NMR (500 MHz, $CDCl_3$) δ: 10.32 (s, 1H), 7.62 (d, J=8.0 Hz, 1H), 7.38 (d, J=8.4 Hz, 1H), 7.31 (t, J=7.1 Hz, 1H), 7.16-7.11 (m, 1H), 4.23 (t, J=6.7 Hz, 2H), 4.05 (s, 3H), 3.51 (q, J=6.4 Hz, 2H), 2.09 (s, 3H), 1.96 (p, J=6.3 Hz, 2H) ppm;

$^{13}C$ NMR (125 MHz, $CDCl_3$) δ: 185.19, 171.22, 160.61, 137.56, 136.73, 127.16, 125.28, 123.80, 119.20, 113.88, 111.12, 62.08, 36.80, 33.05, 28.42, 20.99 ppm.

Example 2: Preparation of propyl 3-[(3-formyl-1-methyl-1H-indole-2-carbonyl)amino]acetate (Compound 1-2)

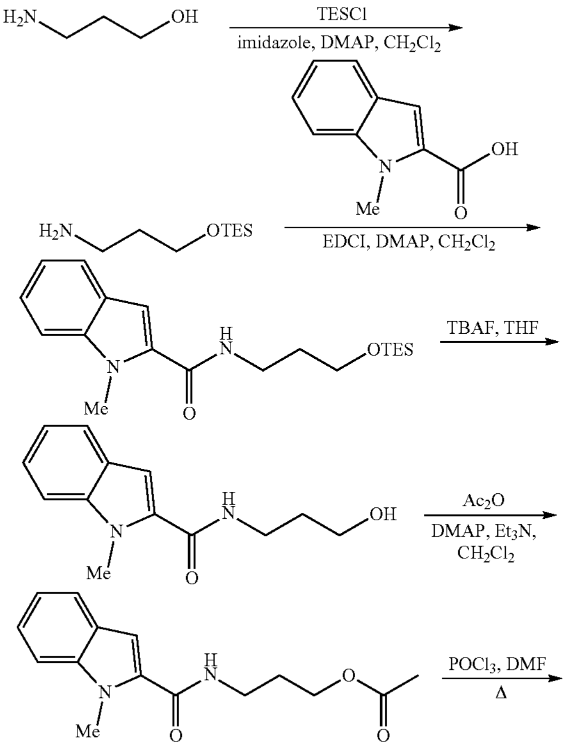

-continued

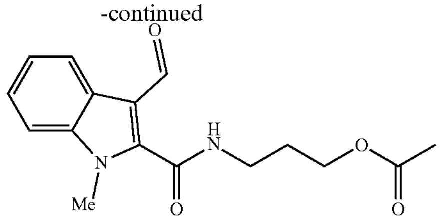

Step 1: Protection of the Hydroxyl Group of 3-Aminopropanol

3-Aminopropanol (375.5 mg, 5 mmol, 1 eq.) was dissolved in anhydrous $Ch_2Cl_2$, followed by adding imidazole and 4-dimethylaminopyridine (DMAP), and finally triethylchlorosilane (TESCl, 1.26 mL, 7.5 mmol, 1.5 eq.) was added thereto under stirring at room temperature, and the reaction was monitored by TLC until it was complete; saturated $NH_4Cl$ solution was added to thus obtained mixture drop by drop to quench the reaction, and then the mixture was extracted with ethyl acetate (EtOAc), the organic phases were combined, washed with a small amount of saturated brine, and then dried with anhydrous $Na_2SO_4$, filtered, concentrated, and purified by column chromatography to give 3-triethylsilyloxy-l-propanamine;

Step 2: Condensation of 3-triethylsilyloxy-1-propylamine with 1-methyl-2-indolecarboxylic acid 1-methyl-2-indolecarboxylic acid (1000 mg, 5.75 mmol, 1.2 eq) was dissolved in anhydrous $CH_2Cl_2$, 1-(3-dimethylaminopropyl)-3-ethylcarbodiimide hydrochloride (EDCI) was dissolved in anhydrous $CH_2Cl_2$, 3-triethylsilyloxy-1-propanamine and DMAP was dissolved in anhydrous $CH_2Cl_2$, respectively, and then the three solutions were mixed. Thus obtained mixture was stirred and reacted under an ice bath and then reacted at room temperature, and the reaction was monitored by TLC until it was complete. The reaction system was extracted with $CH_2Cl_2$, and the lower layer solution was collected and dried by anhydrous $Na_2SO_4$ overnight, filtered, concentrated, and purified by column chromatography to give a product of this step;

Step 3: Deprotection of Hydroxyl Group

The compound obtained above was dissolved in anhydrous tetrahydrofuran (THF), tetrabutylammonium fluoride (TBAF, 1355.4 mg, 5.18 mmol, 1.2 eq.) was added thereto under stirring at room temperature and the reaction was monitored by TLC unit it was complete. the reaction was quenched by adding saturated $NH_4Cl$ solution drop by drop, the mixture was extracted with EtOAc, and the organic phases were combined, washed with a small amount of saturated brine, dried with anhydrous $Na_2SO_4$, filtered, concentrated, and purified by column chromatography to give the product of this step;

Step 4: Esterification of Hydroxyl Group at the End of the Carbon Chain

Under anhydrous conditions, the product obtained above was dissolved in anhydrous $CH_2Cl_2$ at room temperature under stirring. Then triethylamine ($Et_3N$) and DMAP were added successively at room temperature, and finally the reaction was initiated by adding acetic anhydride ($Ac_2O$, 0.59 mL, 6.3 mmol, 1.5 eq.) drop by drop. The reaction process was monitored by TLC and the reaction was complete after about 40 minutes. The reaction was quenched by adding saturated $NH_4Cl$ solution drop by drop, thus obtained mixture was extracted with EtOAc, and the organic phases were combined, washed with a small amount of saturated brine, dried with anhydrous $Na_2SO_4$, filtered, concentrated, and purified by column chromatography to give the product of this step;

Step 5: Introduction of Aldehyde Group on No. 3 Carbon Atom of Indole by Using Vilsmeier-Haack Reaction Firstly, under anhydrous and oxygen-free conditions at 0° C., DMF and $POCl_3$ were mixed and stirred at 0° C. for 30 min, and then the ice-water bath was withdrawn, and the mixing and stirring continued for another 30 min to give disubstituted formamide-phosphorochloride required for the reaction. Under anhydrous and oxygen-free conditions, DMF was added drop by drop to dissolve the product obtained above at 0° C. The dissolved feedstock was then added to the prepared disubstituted formamide-phosphorochloride drop by drop, and the environment of 0° C. was maintained while dropping. When the addition was complete, the ice water bath was removed and the temperature gradually increased to 50° C. to continue the reaction. The reaction was monitored by TLC and the reaction was complete after about 5 hours. A small amount of methyl tertiary butyl ether (MTBE) was then added to dilute the reaction system, followed by adding a small amount of distilled water to quench the reaction and continuous stirring for about 30 minutes. The mixture was extracted with EtOAc, and the organic phases were combined, washed with a small amount of saturated brine, dried with anhydrous $Na_2SO_4$, filtered, concentrated, and purified by column chromatography to give 107.52 mg of product (0.36 mmol) with a total yield of 36%.

Example 3: Preparation of propyl 3-[(3-formyl-1-methyl-1H-indole-2-carbonyl)amino]benzoate (Compound 2-1)

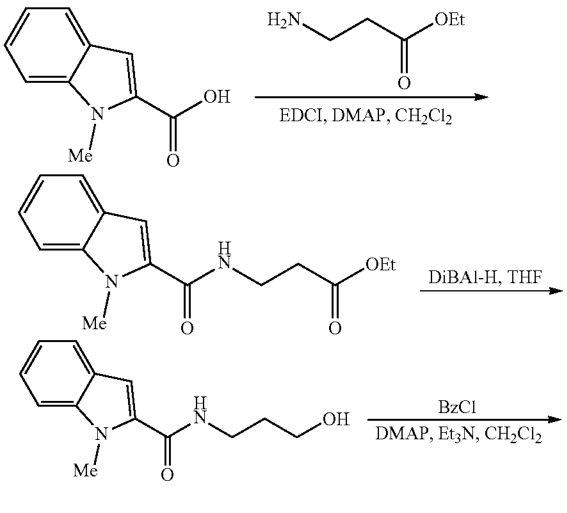

-continued

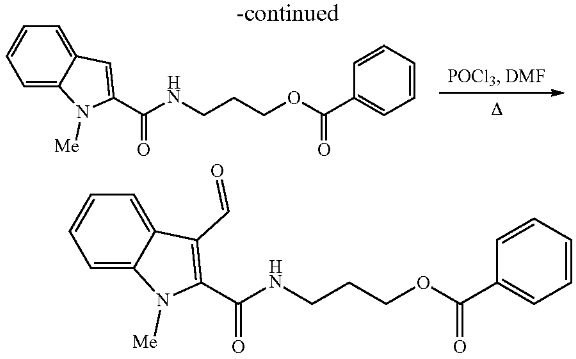

Step 1: Preparation of ethyl 3-[(1-methyl-1H-indole-2-carbonyl)amino]propanoate

Under anhydrous conditions, 1-methyl-2-indolecarboxylic acid (588 mg, 3.36 mmol, 1 eq.) was dissolved in anhydrous dichloromethane ($CH_2Cl_2$, 10 mL) at 0° C. under stirring, followed by adding solid DMAP (715.68 mg, 5.71 mmol, 1.7 eq.) in powder form and solid EDCI (730.8 mg, 3.70 mmol, 1.1 eq.), and finally the reaction was initiated by adding β-alanine ethyl ester hydrochloride powder (586.32 mg, 3.70 mmol, 1.1 eq.). The reaction was monitored by TLC. After natural melting of the ice water bath, the reaction was allowed to continue at room temperature for approximately 12 hours until it was complete. Saturated ammonium chloride ($NH_4Cl$) solution was then added drop by drop to quench the reaction. Thus obtained mixture was extracted with ethyl acetate (EtOAc), and the organic phases were combined, washed with saturated brine, dried with anhydrous sodium sulfate ($Na_2SO_4$), and left to stand for a few moments, then evaporated and concentrated to obtain a crude product, which was purified by column chromatography to obtain 840 mg (3.02 mmol) of ethyl 3-[(1-methyl-1H-indole-2-carbonyl)amino]propanoic acid derivatives with a yield of 90%.

Step 2: Reduction of the Terminal Ester Group of the Compound to a Hydroxyl Group Under anhydrous and oxygen-free conditions, the product obtained above (807.82 mg, 2.6 mmol, 1 eq.) was dissolved in anhydrous tetrahydrofuran (THF, 15 mL) at 0° C. under stirring, followed by adding Diisobutylaluminium hydride (DIBAl-H, 10.4 mL) at a concentration of 1 mol/L drop by drop thereto and the reaction was carried out at 0° C. The reaction was monitored by TLC (petroleum ether/ethyl acetate=1:1) until it was complete after 1.5 hours. Then methanol (MeOH, 5 mL) was added drop by drop to quench the reaction, followed by adding a small amount of methyl tertiary-butyl ether (MTBE) to dilute the reaction system, and saturated sodium potassium tartrate solution to further quench the reaction, and stirring was continued until the reaction system was clarified. After clarification, thus obtained mixture was extracted with EtOAc, the organic phases were combined, washed with a small amount of saturated brine, and then dried with anhydrous $Na_2SO_4$, left to stand for a few moments and then concentrated by rotary evaporation to give a crude product which was purified by column chromatography to give 307.32 mg (1.12 mmol) of product with a yield of 44%.

Step 3: Esterification of Hydroxyl Groups at the End of the Carbon Chain

Under anhydrous conditions, a total of 296.9 mg (1.10 mmol, 1 eq.) of the product obtained above was dissolved in anhydrous $CH_2Cl_2$ (10 mL) at room temperature under stirring, followed by successively adding triethylamine ($Et_3N$, 0.30 mL, 2.20 mmol, 2 eq.) and DMAP (13.75 mg, 0.11 mmol, 0.1 eq.) at room temperature, and finally the reaction was initiated by adding benzoyl chloride (BzCl, 0.38 mL, 3.30 mmol, 3 eq.) drop by drop. The reaction was monitored by TLC until it was complete after about 40 minutes. The reaction was quenched by adding saturated $NH_4Cl$ solution drop by drop, thus obtained mixture was extracted with EtOAc, the organic phases were combined, washed with a small amount of saturated brine, and then dried with anhydrous $Na_2SO_4$, left to stand for a few moments and then concentrated by rotary evaporation to give a crude product which was purified by column chromatography to give 299.5 mg (0.89 mmol) of product with a yield of 80%.

Step 4: Introduction of Aldehyde Group on No. 3 Carbon Atom of Indole by Using Vilsmeier-Haack Reaction Firstly, under anhydrous and oxygen-free conditions at 0° C., DMF (3 mL) and $POCl_3$ (0.12 mL) were mixed and stirred at 0° C. for 30 min, and then the ice-water bath was withdrawn, and the mixing and stirring continued for another 30 min to give disubstituted formamide-phosphorochloride required for the reaction. Under anhydrous and oxygen-free conditions, DMF (3 mL) was added drop by drop to dissolve 286.0 mg (0.86 mmol, 1 eq.) of the product obtained above at 0° C. The dissolved feedstock was then added to the prepared disubstituted formamide-phosphorochloride drop by drop, and the process was repeated twice with DMF (1.5 mL). When the addition was complete, the ice water bath was removed and the temperature gradually increased to 50° C. to continue the reaction.

The reaction was monitored by TLC until it was complete after about 5 hours. A small amount of methyl tertiary butyl ether (MTBE) was then added to dilute the reaction system and the reaction was quenched by adding a small amount of distilled water with continuous stirring for about 30 minutes. Thus obtained mixture was extracted with EtOAc, the organic phases were combined, washed with a small amount of saturated brine, and then dried with anhydrous $Na_2SO_4$, left to stand for a few moments and then concentrated by rotary evaporation to give a crude product which was purified by column chromatography to give 139.2 mg (0.38 mmol) of product with a yield of 45%.

Molecular formula: $C_{21}H_{20}N_2O_4$; Molecular weight: 364.14, ESI-MS m/z: 387.13138 $[M+Na]^+$; $^1H$ NMR (500 MHz, $CDCl_3$) δ: 10.32 (s, 1H), 8.09-7.97 (m, 4H), 7.42-7.31 (m, 5H), 4.50 (t, J=6.2 Hz, 2H), 4.21 (s, 3H), 3.84 (s, 1H), 3.69 (t, J=6.1 Hz, 2H), 2.22-2.18 (m, 2H) ppm;

$^{13}C$ NMR (125 MHz, $CDCl_3$) δ: 185.21, 166.50, 160.45, 137.20, 132.84, 129.98, 129.46, 128.21, 124.93, 123.48, 119.48, 114.07, 110.74, 62.47, 36.92, 32.47, 28.48 ppm.

In the following Examples, the control compound is 3-[(1-methyl-1H-indole-2-carbonyl)amino]propionic acid, which is the most active indole analogue disclosed in CN2019107285315 and has the following structure:

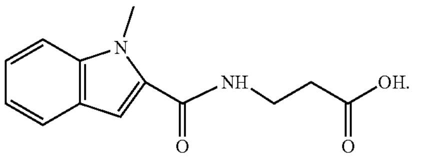 [SMILES: Cn1c(C(=O)NCCC(=O)O)cc2ccccc21]

Example 4: Evaluation of Stability of the Compounds of Present the Invention

The stability of compounds 1-1, 2-1 and the indole analogue 3-[(1-methyl-1H-indole-2-carbonyl) amino]propionic acid disclosed in CN2019107285315 was tested by experiments at high temperature and high humidity. The compounds were placed in 24-well plates, spread as a thin layer with a thickness of no more than 5 mm and placed in an oven at 60° C. for 10 days. Observation of appearance, TLC identification and determination of absorbance were carried out on the 5th day and the 10th day, respectively, in order to compare with the samples on the 0th day. An amount of compounds were taken into tightly closed brown colored penicillin bottles (the compounds were spread as a thin layer with a thickness of no more than 5 mm) and then placed into a tightly closed container with saturated NaCl solution and left at room temperature away from light for 10 days. Observation of appearance, TLC identification and determination of absorbance were carried out on the 5th day and the 10th day, respectively, in order to compare with the samples on the 0th day.

The residual content of compound 1-1 after 5 and 10 days in a high temperature environment was 95.4±08% and 94.2±0.6%, respectively, and the residual content of compound 1-1 after 5 and 10 days in a high humidity environment was 93.5±0.4% and 90.7±0.3%, respectively. The residual content of compound 2-1 after 5 and 10 days in a high temperature environment was 93.6±0.6% and 91.7±0.5%, respectively, and the residual content of compound 2-1 after 5 and 10 days in a high humidity environment was 94.2±0.3% and 90.1±0.8%, respectively. The residual content of the indole analogue 3-[(1-methyl-1H-indole-2-carbonyl) amino]propionic acid disclosed in CN2019107285315 after 5 and 10 days in a high temperature environment was only 23.1±0.1% and 4.2±0.1%, respectively, and the residual content after 5 and 10 days in a high humidity environment was only 29.5±0.1% and 8.8±0.1%, respectively. The above results show that the compounds of the present invention are obviously more stable than the indole analogue 3-[(1-methyl-1H-indole-2-carbonyl)amino]propanoic acid disclosed in CN2019107285315.

The above experimental results show that the indole analogue disclosed in CN2019107285315 has poor stability. Whereas, the stability of the compounds of the present invention is significantly enhanced, the pharmaceutical ingredients do not change significantly, the therapeutic effect will be stable, long-lasting and easy to become a medicament.

Example 5: In Vitro Binding of TRPC6 Protein to the Compounds of the Present Invention The binding ability of the compounds of the present invention (as exemplified by the compounds obtained in Examples 1 to 3) to the TRPC6 protein was determined using the microscale thermophoresis (MST) method. The method was as follows:

Preparation and labelling of protein solution: TRPC6 protein dry powder (Alomone Labs, Israel) was prepared into a protein mother solution at a concentration of 10 μM using PBS-Buffer, and 35 μL of the protein stock solution was taken to the Buffer exchange A column, and centrifuged to obtain the Tris-removed protein. 34 μL Labelling Buffer was added to the Tris-removed protein according to the instructions of the Protein Fluorescent Labelling Kit (model L001). After mixing well, 3 μL of NT-647-NHS fluorescent dye was added and thus obtained mixture was incubated for 20 minutes. The protein-dye mixture was transferred to the purification B column, 300 μL of PBS-Buffer was added, and the target protein, i.e. fluorescent labelled protein TRPC6, was collected by centrifugation (with a final concentration of about 2 μM). 180 μL of target protein was mixed with 1620 μL of PBS-Buffer, and then 9 μl of Tween-20 were added thereto. Thus the resulting mixture was mixed and then centrifuged to obtain the target protein solution.

Preparation of compound solutions: the compounds were prepared separately with DMSO to storage solutions with a concentration of 10 μM. 10 μL of each storage solution was placed in a 0.2 μL EP tube, 90 μL of PBS was added thereto and the resulting mixture was thoroughly mixed to prepare 100 μL of working solution at a concentration of 1 μM for later use. Ligand gradient dilutions were made for a total of 16 concentrations, and 10 μL of 10% DMSO-Buffer was added to each of the 15 gradients except gradient 1, followed by the addition of 10 μL of ligand working solution to gradients 1 and 2, respectively. The liquid in tube 2 was mixed and then 10 μL therein was taken into tube 3, and dilution was carried out in this manner until tube 16. Tube 16 was mixed and 10 μL therein was taken and discarded, and the remainder was kept for later use.

Detection and analysis: 10 μL of protein solution was added to the 16 compound gradient dilutions respectively and mixed, and the resultant mixtures were transferred to capillary tubes sequentially to start detection on machine. After loading the data, the MST analysis model and Kd Model were selected to obtain the fitting curve and dissociation constant (Kd).

Results: the collected data was analyzed to obtain Kd for binding TRPC6 protein to compounds 1-1 and 2-1 obtained in Examples 1 and 3 of the present invention as 11.99±3.61 μM and 19.00±3.15 μM, whereas the Kd for the indole analogue 3-[(1-methyl-1H-indole-2-carbonyl)amino]propionic acid disclosed in CN2019107285315 is 29.78±0.26 μM. The above results show that the compounds of the present invention all have significant affinity with the TRPC6 protein and have a stronger affinity than the indole analogues disclosed in CN2019107285315.

Example 6: Specific Binding of the Compounds of the Present Invention to TRPC6 Protein The binding ability of the compounds of the present invention (as exemplified by the compounds 1-1 and 2-1 obtained in Examples 1 and 3) for other TRPC proteins (e.g., TRPC1, TRPC3, TRPC4, TRPC5, and TRPC7) was determined using the microscale thermophoresis (MST) method. The method was as follows:

The affinity of the compounds of the present invention with TRPC1, TRPC3, TRPC4, TRPC5 and TRPC7 proteins, respectively, was determined by the same method as in Example 5.

Results: the Kd values for binding compounds 1-1 and 2-1 obtained in Examples 1 and 3 to TRPC4 and TRPCS proteins cannot be measured, i.e., there was no significant binding. The Kd values for binding compound 1-1 to TRPC1, TRPC3 and TRPC7 proteins were 2.94 μM, 970.17 μM and 3.04 μM, respectively; the affinity strengths of compound 1-1 to TRPC6 protein were 245-fold, 81-fold and 254-fold higher than those of compound 1-1 to TRPC1, TRPC3 and TRPC7 proteins, respectively. The Kd values for binding compound 2-1 obtained in Example 3 to TRPC1, TRPC3 and TRPC7 proteins were 2.40 μM, 1.40 μM and 3.21 μM, respectively; the affinity strengths of compound 2-1 to TRPC6 protein were 155-fold, 51-fold and 160-fold higher than those of compound 2-1 to TRPC1, TRPC3 and TRPC7 proteins, respectively.

The Kd values for binding the indole analogue 3-[(1-methyl-1H-indole-2-carbonyl)amino]propionic acid disclosed in CN2019107285315 to TRPC1, TRPC3 and TRPC7 proteins were 1.94 μM, 812.17 μM and 1.04 μM, respectively; the affinity strengths of this compound to TRPC6 protein were 65-fold, 27-fold and 35-fold higher than those of this compound to TRPC1, TRPC3 and TRPC7 proteins, respectively.

The above results show that the compounds of the present invention have high specificity for binding to TRPC6 protein, and the binding selectivity of the compounds of the present invention for TRPC6 protein is significantly higher than that of the indole analogue disclosed in CN2019107285315.

Example 7: Inhibition of TRPC6 Channel-Mediated $Ca^{2+}$ Entry by Compounds of the Present Invention The inhibitory effect of the compounds of the present invention (as exemplified by Compound 1-1 obtained in Example 1) on TRPC6 channel-mediated $Ca^{2+}$ entry was determined using $HEK293_{hTRPC6}$ as a tool cell overexpressing TRPC6 protein. The method was as follows:

Establishment of $HEK293_{hTRPC6}$, a tool cell overexpressing TRPC6 protein: human embryonic kidney cells HEK293 were placed in DMEM culture medium (containing 10% inactivated fetal bovine serum, 100 U-mL$^{-1}$ penicillin, and 100 mg-L$^{-1}$ streptomycin) and cultured at 37° C. in a 5% $CO_2$ incubator. Cells in the logarithmic growth phase were harvested at 50% and incubated with 25 μL of LV105-TRPC6 lentiviral particle suspension for 24 hours, and then the medium was changed. The experiment included a negative control group (no-load lentivirus) and a blank control group. The medium containing 2 μg/mL puromycin was changed after 48 h of infection until the cells in the blank group died. Western Blot assay was performed to detect the expression of TRPC6 protein in the cells to verify the successful construction of $HEK293_{hTRPC6}$ cell.

Determination of the effect of the compounds on changes in intracellular calcium ion concentration ($[Ca^{2+}]_i$) in $HEK293_{hTRPC6}$ cells: $HEK293_{hTRPC6}$ cell suspension was added to a 24-well plate with a coverslip and incubated at 37° C. in a 5% CO2 incubator for 24 h. The cell crawls were then removed and placed in the fluorescent dye Fura-2/AM, and incubated for 20 min at room temperature away from light. The slides were placed in the center of the bath, perfused with calcium-free Tyrode's solution for 5 min and fixed on the stage of an inverted fluorescence microscope. A solution of the compound of the present invention at 80 μM was added to the bath and the cells were preincubated for 5 min, to which 1-Oleoyl-2-acctyl-sn-glycerol (OAG) at 80 μM was added to activate the TRPC6 channels and $Ca^{2+}$ at 2 μM was added. Fluorescence intensity was measured at different excitation wavelengths (340 nm, 380 nm) using a TILL Ion Imaging system (TILLvisION), and the value of fluorescence intensity emitted by intracellular fluorescent probe at different excitation wavelengths was substituted into the formula: $[Ca^{2+}]_i = Kd \times \beta \times (R-R_{min})/(R-R_{max})$. In the formula, R represents the experimentally determined fluorescence ratio (F340/F380); Kd represents the dissociation constant for the reaction of Fura-2/AM with $Ca^{2+}$, which is 386 nmol/L under physiological conditions; $R_{max}$ represents the F340/F380 when $Ca^{2+}$ is saturated (all Fura-2/AM is bound to $Ca^{2+}$); $R_{min}$ represents the F340/F380 when there is no $Ca^{2+}$; and β represents the ratio of fluorescence intensities at 380 nm in the absence of $Ca^{2+}$ and when $Ca^{2+}$ is saturated.

Experimental results: the amount of TRPC6-mediated $Ca^{2+}$ entry under conditions of open TRPC6 channels and the presence of extracellular $Ca^{2+}$ was measured, and the actual biological activity of the compounds was assessed by comparison with the solvent control.

The calculation results show that compound 1-1 of the present invention inhibited $Ca^{2+}$ entry into the cells via TRPC6 channels by 79.88% compared with the solvent control group (0.06±0.01 vs. 0.30±0.01, P<0.01), whereas the indole analogue 3-[(1-methyl-1H-indole-2-carbonyl) amino]propionic acid disclosed in CN2019107285315 inhibited $Ca^{2+}$ entry into the cells via TRPC6 channels by 53.92% compared with the solvent control group (0.10±0.01 vs. 0.22±0.01). It shows that the inhibitory effect of the compounds of the present invention on calcium ion entry is significantly stronger than that of the indole analogue disclosed in CN2019107285315; and the compounds of the present invention also have stronger therapeutic effect on hypertension and cardiac arrhythmia, etc., caused by calcium ion entry.

Example 8: Half Maximal Inhibitory Concentrations of the Compounds of the Present Invention on TRPC6 Channel-Mediated $Ca^{2+}$ Entry The half maximal inhibitory concentrations ($IC_{50}$) of the compounds of the present invention (as exemplified by Compound 1-1 obtained in Example 1) on TRPC6 channel-mediated $Ca^{2+}$ entry were determined using $HEK293_{hTRPC6}$, a tool cell overexpressing TRPC6 protein. Methods were as follows: $HEK293_{hTRPC6}$, a tool cell overexpressing TRPC6 protein, was established in the same manner as in Example 7.

Determination of the effect of compounds on changes in intracellular calcium ion concentration in $HEK293_{hTRPC6}$ cells: the mother solution of the compounds was diluted to the following concentrations, 0.1 nM, 0.3 nM, 1 nM, 3 nM, 10 nM, 30 nM, 100 nM, 300 nM, 1,000 nM, and 3,000 nM, respectively, using cell culture medium. $HEK293_{hTRPC6}$ cell suspension was added to a 24-well plate with coverslips and incubated at 37° C., 5% $CO_2$ incubator for 24 h. The cell crawls were removed and placed in fluorescent dye Fura-2/AM and incubated at room temperature away from light for 20 min. The crawls were placed in the center of the bath, perfused with calcium-free Tyrode's solution for 5 min and fixed on the stage of an inverted fluorescence microscope. 1-Oleoyl-2-acctyl-sn-glycerol (OAG) at 80 μM was added to activate the TRPC6 channels and $Ca^{2+}$ at 2 mM was added.

Fluorescence intensity was measured at different excitation wavelengths (340 nm, 380 nm) using a TILL Ion Imaging System (TILLvisION), and the value of fluorescence intensity emitted by intracellular fluorescent probe at different excitation wavelengths was substituted into the formula: $[Ca^{2+}]_i$=Kd×β×(R−$R_{min}$)/(R−$R_{max}$). In the formula, R represents the experimentally determined fluorescence ratio (F340/F380); Kd represents the dissociation constant for the reaction of Fura-2/AM with $Ca^{2+}$, which is 386 nmol/L under physiological conditions; $R_{max}$ represents the F340/F380 when $Ca^{2+}$ is saturated (all Fura-2/AM is bound to $Ca^{2+}$); $R_{min}$ represents the F340/F380 when there is no $Ca^{2+}$; and represents the ratio of fluorescence intensities at 380 nm in the absence of $Ca^{2+}$ and when $Ca^{2+}$ is saturated. Each concentration was repeated 3 times and about 10 cells were selected from each cell crawler. Dose-effect curves were fitted using GraphPad Prism software and the $IC_{50}$ was calculated.

Experimental results: Compound 1-1 obtained in Example 1 showed good concentration-dependent inhibition of TRPC6 channel-mediated $Ca^{2+}$ entry, with a calculated $IC_{50}$ of 11.43 nM, whereas the $IC_{50}$ of the indole analogue 3-[(1-methyl-1H-indole-2-carbonyl)amino]propionic acid disclosed in CN2019107285315 for TRPC6 channel-mediated $Ca^{2+}$ entry was 24.1 nM. It shows that the compounds of the present invention have a significantly stronger inhibitory effect on $Ca^{2+}$ entry than the indole analogue disclosed in CN2019107285315. At the same concentration, the inhibitory effect of the compounds of the present invention on TRPC6 channel-mediated $Ca^{2+}$ entry is twice as great as that of the indole analogue 3-[(1-methyl-1H-indole-2-carbonyl)amino]propionic acid disclosed in CN 2019107285315 with the best activity.

Example 9: Therapeutic Effect of the Compounds of the Present Invention on Focal Segmental Glomerulosclerosis The therapeutic effect of the compounds of the present invention (as exemplified by Compound 1-1 obtained in Example 1) on nephropathy was determined using a mouse model of focal segmental glomerulosclerosis. The method was as follows:

Grouping of animals: 40 male Balb/c mice aged 8 weeks were randomly divided into 8 groups: a control group, a model group, a treatment group of low-dose compound 1-1 (10 mg/kg) (adriamycin), a treatment group of medium-dose compound 1-1 (25 mg/kg) (adriamycin), a treatment group of high-dose compound 1-1 (50 mg/kg) (adriamycin), a treatment group of medium-dose indole analogue 3-[(1-methyl-1H-indole-2-carbonyl)amino]propionic acid disclosed in CN2019107285315 (25 mg/kg) (adriamycin), a positive control group (irbesartan, 50 mg/kg) (adriamycin) and a normal animal treatment group (50 mg/kg), with 5 mice in each group, housed in animal room with 12 hours light/12 hours dark. Each mouse in the model group, the treatment groups and the positive control group was injected once into the tail vein with adriamycin at a dose of 8 mg/kg, and each mouse in the control group was injected once into the tail vein with saline at the same dose. The mice in the control group and model group were administered equal amount of saline by gavage for 6 weeks, and the mice in other group were administered corresponding compound in doses by gavage at a fixed time each day for 6 weeks after modelling with adriamycin. The body weights were recorded weekly and urine samples were collected.

Collection of urine samples: animals were placed in separate metabolic cages by group on days 0, 7, 14, 21, 28, 35, and 42 after modelling, with free access to water and no access to food, and urine samples were collected from each group of mice.

Determination of urine protein level using Coomassie brilliant blue (CBB) method: urine protein level was determined by urine protein quantitative test kit (Nanjing Jiancheng Bioengineering Institute). CBB working solution was prepared according to the kit instructions. 0.05 mL of each urine sample was mixed with 3 mL of CBB working solution, the mixture was allowed to stand for 5 min, and the absorbance value of each sample was determined at 595 nm. The urine protein levels samples of each group was calculated according to the protein standardization formula: urine protein level (mg/L)=(measured OD−blank OD)/(standard OD−blank OD)×563 mg/L.

Collection of serum samples: orbital blood from each mouse was collected in an EP tube, placed at 37° C. for 20 minutes, and centrifuged to obtain an upper layer of serum.

Collection of plasma samples: orbital blood from each mouse was collected in an anticoagulation tube, mixed well and stored at 4° C. for later use.

Determination of urea nitrogen level in plasma by diacetyl monoxime method: urea nitrogen level was determined by using blood urea nitrogen (BUN) test kit (Nanjing Jiancheng Bioengineering Institute). According to the kit instructions, 0.05 mL of anticoagulated plasma sample was mixed with 1 mL of oxime solution and 1 mL of acid working solution, and the mixtures were placed in a boiling water bath for 15 minutes. A UV-visible spectrophotometer was used to determine the absorbance values of each tube at a wavelength of 520 nm. Urea nitrogen levels in plasma samples of each group were calculated according to the formula: Urea nitrogen level (mmol/L)=(measured OD value−blank OD value)/(standard OD value−blank OD value)×10 mmol/L.

Collection of kidney tissue samples: kidneys were taken from mice after anesthesia, cut horizontally, and the upper part of the kidneys was embedded in OCT embedding box, sliced with frozen slicer and stored at −20° C.

H&E staining was used to assess pathological glomerular changes, and the procedure was as follows: frozen sections were fixed with 95% ethanol for 2 minutes, hydrated with distilled water, stained with hematoxylin for 3 minutes, washed with distilled water for 3 minutes, differentiated using 1% hydrochloric acid in ethanol for 10 seconds, washed with distilled water for 30 seconds, returned to blue in running water for 5 minutes, washed in distilled water for 30 seconds, stained with eosin for 30 seconds, washed with 75% and 85% ethanol for 20 seconds each, dehydrated rapidly with 95% ethanol for 1 minute, dehydrated with anhydrous ethanol, cleared to transparency in xylene (1 minute×3), and finally sealed with neutral balsam and photographed with a biomicroscope.

Evaluation of lesions in the glomerular mesangial areas or basement membranes areas by PAS staining: the procedure was as follows, Frozen sections were washed in distilled water, oxidized in periodic acid solution for 10 minutes and then rinsed thoroughly with tap water; the samples were immersed in Schiff s reagent for 30 minutes and rinsed in tap water for 10 minutes; stained in hematoxylin staining solution for 3 minutes and rinsed in tap water for 15 minutes, dehydrated with 95% ethanol and anhydrous ethanol, cleared to transparency in xylene, and finally sealed with neutral balsam, and photographed with a biomicroscope.

Data statistics and analysis: SPSS22.0 software was used for data analysis, all data were expressed as mean±standard error (mean±SEM), two-sample t-test was used to compare means between two groups; one-way ANOVA was used to compare means between multiple groups, and Turkey's method was used to compare two groups. A significance level of $P<0.05$ indicates a statistically significant difference between groups.

Experimental results: (1) Compared with the control group, the body weight of mice in the model group decrease by 15.8% (29.9±0.6 g vs. 25.2±0.8 g, $P<0.01$); in the treatment group of low-dose compound 1-1 obtained in Example 1, the treatment group of medium-dose compound 1-1 and the treatment group of high-dose compound 1-1, and the treatment group of medium-dose indole analogue 3-[(1-methyl-1H-indole-2-carbonyl)amino]propanoic acid disclosed in CN2019107285315, and the positive control group (irbesartan), the mice have increased body weights compared with those in the FSGS group, indicating that compound 1-1 obtained in Example 1 ameliorated FSGS-induced body weight loss in mice.

(2) Urine protein level and serum urea nitrogen level are the main clinical indexes of proteinuria. In FSGS, renal function is severely impaired, with increased urine protein level and serum urea nitrogen level. Compared with the blank control group, the urine protein level and the serum urea nitrogen level are increased by 390.1% and 82.3%, respectively, in the model group (urine protein level: 547.0±106.3 mg/mL vs. 111.6±7.27 mg/mL, $P<0.01$; urea nitrogen level: 16.08±0.23 mmol/L vs. 8.82±0.17 mmol/L, $P<0.001$). Urine protein level is reduced by 30.2% (382.0±80.77 mg/mL vs. 547.0±106.3 mg/mL, $P<0.01$) and serum urea nitrogen level is reduced by 9.0% (14.63±0.19 mmol/L vs. 16.08±0.23 mmol/L, $P<0.001$) in the positive control group (irbesartan) compared with the model group. Urine protein level and serum urea nitrogen level are significantly reduced in the treatment group of low-dose compound 1-1, the treatment group of medium-dose compound 1-1 and the treatment group of high-dose compound 1-1, wherein compared with the model group, urine protein level is reduced by 28.6% (390.5±74.6 mg/mL vs. 547.0±106.3 mg/mL, $P<0.01$) and serum urea nitrogen level is reduced by 27.2% (11.7±0.33 mmol/L vs. 16.08±0.23 mmol/L, $P<0.001$) in the treatment group of medium-dose compound 1-1 (25 mg/kg); and urine protein level is reduced by 42.7% (312.7±57.57 mg/mL vs. 547.0±106.3 mg/mL, $P<0.001$) and serum urea nitrogen level is decreased by 29.8% (11.29±0.40 mmol/L vs. 16.08±0.23 mmol/L, $P<0.001$) in the treatment group of high-dose compound 1-1 (50 mg/kg), indicating that the effect of compound 1-1 is significantly stronger than that of the positive control drug. In comparison, in the treatment group of medium-dose indole analogue 3-[(1-methyl-1H-indole-2-carbonyl)amino]propionic acid (25 mg/kg) disclosed in CN2019107285315, urine protein level is reduced by 22.6% (423.4±64.7 mg/mL vs. 547.0±106.3 mg/mL, $P<0.01$), and serum urea nitrogen level is reduced by 20.3% (12.82±0.46 mmol/L vs. 16.08±0.23 mmol/L, $P<0.05$), indicating that this compound is significantly less potent than compound 1-1 of the present invention at the same dose. The above results indicate that compound 1-1 also significantly inhibits the increase of urine protein level as well as serum urea nitrogen level in the mouse model of FSGS, and the therapeutic effect on the mouse model of FSGS is significantly stronger than that of the indole analogue 3-[(1-methyl-1H-indole-2-carbonyl)amino]propionic acid disclosed in CN2019107285315 at the same dose.

(3) Compound 1-1 obtained in Example 1 significantly ameliorates glomerular lesions caused by FSGS. Pathological analysis results of renal tissue stained with H&E stain, PAS stain and Sirius red stain (FIG. 1 shows FSGS-induced renal tissues after treatment with compound 1-1 of the present invention, which are stained with hematoxylin-eosin stain, periodic acid-schiff stain and Sirius red stain, respectively, wherein compound 0-1 is 3-[(1-methyl-1H-indole-2-carbonyl)amino]propionic acid) are shown in FIG. 1. Compared with the mice in the blank control group, glomerular mesangial matrix proliferation, podocyte hyperplasia and adhesions, hyalinization of tubular wall, and obvious focal segmental sclerosis are observed in mice in the model group of FSGS; compound 1-1 of the present invention significantly alleviates the proliferation of the glomerular mesangial matrix, with a reduction in the number of podocyte hyperplasia and adhesions, and hyalinization of tubular wall and focal segmental sclerosis are not observed; and the positive control (irbesartan) group shows the same effect. In contrast, in the treatment group of medium-dose indole analogue 3-[(1-methyl-1H-indole-2-carbonyl)amino]propanoic acid disclosed in CN2019107285315, glomerular mesangial matrix hyperplasia is reduced compared with the model group, but increased compared with the treatment groups of compound 1-1 of the present invention. The above results show that the compounds of the present invention can significantly ameliorate FSGS-induced glomerular lesions and delay the development of the disease, and the therapeutic effect on focal segmental glomerulosclerosis is significantly stronger than that of the indole analogues disclosed in CN2019107285315 at the same dose.

Example 10: Evaluation of the Effect of the Compounds of the Present Invention in a Model of Pulmonary Hypertension Disease The preventive effect of the compounds of the present invention (as exemplified by compound 1-1 obtained in Example 1) on pulmonary hypertension was determined using a rat model of pulmonary hypertension induced by monocrotaline. The method was as follows:

Grouping of animals: 70 male SD rats with weigh of 200±20 g were randomly divided into 7 groups, i.e., a normal control group, a monocrotaline (MCT) model group, a treatment group of low-dose compound 1-1 (10 mg/kg) (MCT), a treatment group of medium-dose compound 1-1 (25 mg/kg) (MCT), a treatment group of high-dose compound 1-1 (50 mg/kg) (MCT), a treatment group of medium-dose indole analogue 3-[(1-methyl-1H-indole-2-carbonyl) amino]propionic acid (25 mg/kg) disclosed in CN2019107285315 (MCT), and a sildenafil group (150 mg/kg) (MCT), with 10 rats in each group.

Experimental procedure: MCT was prepared as a 2% solution with a mixture of ethanol and saline (2:8) and the solution was injected intraperitoneally once at a dose of 60 mg/kg body weight in all groups except the normal control group. Each rat in the normal control group was injected intraperitoneally once with a solution prepared from ethanol and saline in a volume ratio of 2:8. Compound 1-1 obtained in Example 1, the indole analogue 3-[(1-methyl-1H-indole-2-carbonyl)amino]propionic acid disclosed in CN2019107285315, or the positive drug sildenafil was administered by gavage to the mice in the treatment groups on the day of modelling, and saline was administered by gavage to the mice in the normal control group and the MCT model group. The drugs were administered by gavage once a day for 28 days until 12 hours before test.

Determination of hemodynamic indexes: a polyethylene plastic microcatheter filled with heparin solution (0.9% sodium chloride solution+10 U/mL heparin) was inserted into the right external jugular vein of a rat, and the other end of the microcatheter was connected to a miniature pressure transducer to monitor the pressure changes. Under the guidance of the pressure waveform, the microcatheter passed through the superior vena cava into the right atrium, the tricuspid orifice, the right ventricle (RV) and finally into the pulmonary trunk, where the mean pulmonary artery pressure (mPAP) was measured. After 30 minutes of stabilization, the POWERLAB multi-channel intelligent physiological signal acquisition and recording system was applied to acquire, record and analyze the indexes.

Determination of the index of right ventricular (RV) hypertrophy: at the end of the experiment, the heart was removed by dissection of the thorax and the atrial tissue was cut off. The right ventricle (RV), left ventricle (LV), and interventricular septum (S) were isolated along the edge of the interventricular septum, and the RV, LV, and S were weighed after absorbing water with filter paper and the ratio RV/(LV+S) was used to reflect the degree of RV hypertrophy.

Pathological examination of pulmonary vessels: tissue blocks were taken from the same site in the lower lobe of the right lung and fixed in 10% neutral formaldehyde (pH=7.4) for 2 days. Routine paraffin embedding, serial sections, H&E staining and light microscopy were performed to observe morphological changes in small pulmonary arteries.

Effect on inflammatory factors in lung tissue: Lung tissues were collected from each group of rats, homogenates of lung tissue were prepared and centrifuged and supernatants were collected. The protein level in the supernatant was determined by Coomassie brilliant blue method, and tumor necrosis factor-α (TNF-α) in rats was determined by an ELISA kit (Beijing 4A Biotech Co., Ltd.). According to the experimental steps in the manual, the standards and lung tissue samples were added into the corresponding wells (100 μL/well), respectively, and the reaction wells were sealed with sealing tape, incubated at 37° C. for 90 minutes, and the plates were washed; except the blank well, a biotinylated antibody working solution (100 μL/well) was added to the wells, and the reaction wells were sealed with sealing tape, and incubated at 37° C. for 60 minutes and the plates were washed; except the blank well, an enzyme conjugate working solution (100 μL/well) was added to the wells, and the reaction wells were sealed with sealing tapes and incubated at 37° C. for 30 minutes without light, and the plates were washed; a color developing substrate (100 μL/well) was added to the wells, the reaction wells were incubated at 37° C. for 15 minutes without light; a stop solution (100 μL/well) was added, and then the $OD_{450}$ values were determined within 10 minutes after mixing.

Results: the compounds of the present invention significantly ameliorate hemodynamics and right ventricular hypertrophy in the rat model MCT: the changes in mPAP and mCAP of the rats in each group are shown in Table 1. Compared with the mean pulmonary arterial pressure (16.1±2.8 mmHg) of the rats in the normal control group, the mPAP (33.7±4.3 mmHg) of the rats in the model group was significantly higher (P<0.05), indicating that MCT induced significant PAH. Gavage administration of sildenafil significantly inhibits the increase in pulmonary arterial pressure in rats. The mPAP of the rats in the treatment group of low-dose compound 1-1 obtained in Example 1, the treatment group of medium-dose compound 1-1 and the treatment group of high-dose compound 1-1 and the treatment group of medium-dose indole analogue 3-[(1-methyl-1H-indole-2-carbonyl)amino]propanoic acid disclosed in CN2019107285315 is lower than that of the rats in the model group, indicating that the compounds of the present invention can significantly reduce MCT-induced PAH in a clear dose-dependent manner. Compared with the normal control group, the right ventricle of the rats in the model group is significantly hypertrophied, and the right ventricular hypertrophy index, RV/(LV+S), is significantly increased (P<0.05), and the right ventricular hypertrophy index of rats in the treatment group of low-dose compound 1-1, the treatment group of medium-dose compound 1-1, the treatment group of high-dose compound 1-1 and the treatment group of medium-dose indole analogue 3-[(1-methyl-1H-indol-2-carbonyl)amino]propionic acid disclosed in CN2019107285315 is lower than that of the rats in the model group, indicating that the compound could reduce MCT-induced RV/(LV+S) in a dose-dependent manner.

From these indexes, the therapeutic effect of compound 1-1 of the present invention is significantly higher than that of 3-[(1-methyl-1H-indole-2-carbonyl)amino]propionic acid disclosed in CN2019107285315 at the same dose.

Histopathological changes: the small pulmonary arteries of rats in the model group showed obvious lesions, with swelling and degeneration of the endothelial cells, obvious hyperplasia of the intima-media smooth muscle, irregular thickening of the vessel wall and narrowing of the lumen, accompanied by infiltration of inflammatory cells in the wall and periphery. Compared with the model group, the small pulmonary artery lesions of the rat in the treatment groups of compound 1-1 obtained in Example 1 and the treatment group of indole analogue 3-[(1-methyl-1H-indole-2-carbonyl)amino]propionic acid disclosed in CN2019107285315 were significantly reduced with thinning of the wall thickness of the small pulmonary artery, the enlargement of the vessel wall and the reduction of inflammatory cell infiltration in the wall and periphery.

Effect on lung tissue inflammatory factor in: the results of the effect of compound 1-1 obtained in Example 1 on MCT-induced lung tissue inflammatory factor of in rat were shown in Table 2. Compared with the normal control group, the proinflammatory cytokine TNF-α was significantly increased in the lung tissue of rats in the MCT model group (P<0.05), whereas the compounds of the present invention significantly and dose-dependently inhibited the increase of the TNF-α level induced by MCT (P<0.05). Although the indole analogue 3-[(1-methyl-1H-indole-2-carbonyl)amino]propionic acid disclosed in CN2019107285315 can also inhibit the increase of TNF-α level induced by MCT, when administered at a dose of 25 mg/kg, it only reduced TNF-α levels by 37.2% compared with the MCT model, which is much lower than the 58.5% reduction by compound 1-1 of the present invention administered at the same dose of 25 mg/kg. The above results show that the compounds of the present invention can dose-dependently ameliorate monocrotaline-induced pulmonary hypertension in rats, can significantly inhibit small pulmonary arterial lesions and peripheral inflammatory cell infiltration, and delay the process of disease development, and their therapeutic effect on pulmonary hypertension disease is significantly stronger than that of the indole analogues disclosed in CN2019107285315.

TABLE 1

Effect of the compounds of the present invention on hemodynamic indexes and right ventricular hypertrophy index in rat model of MCT

| Group | Number of animals | mPAP/ mmHg | RV/ (LV + S) |
|---|---|---|---|
| Normal control | 10 | 16.1 ± 2.8 | 0.24 ± 0.05 |
| MCT model | 10 | 33.7 ± 4.3* | 0.45 ± 0.03* |
| MCT + compound 1-1 of the present invention (10 mg/kg) | 10 | 26.0 ± 2.8*# | 0.37 ± 0.04*# |
| MCT + compound 1-1 of the present invention (25 mg/kg) | 10 | 25.8 ± 2.5*# | 0.31 ± 0.04*# |
| MCT + compound 1-1 of the present invention (50 mg/kg) | 10 | 20.3 ± 3.0# | 0.28 ± 0.03*# |
| MCT + 3-[(1-methyl-1H-indole-2-carbonyl)amino] propionic acid disclosed in CN2019107285315 (25 mg/kg) | 10 | 28.9 ± 3.4*# | 0.38 ± 0.04*# |
| MCT + sildenafil | 10 | 23.6 ± 3.4*# | 0.32 ± 0.02*# |

*means $P < 0.05$ compared with the normal control group, and
#means $P < 0.05$ compared with the MCT model group.

TABLE 2

Effect of the compounds of the present invention on TNF-α level in lung tissues in rat model of MCT

| Group | Number of animals | TNF-α in lung tissue (g/g protein) |
|---|---|---|
| Normal control | 10 | 0.30 ± 0.05 |
| MCT model | 10 | 0.94 ± 0.07* |
| MCT + compound 1-1 of the present invention (10 mg/kg) | 10 | 0.65 ± 0.08*# |
| MCT + compound 1-1 of the present invention (25 mg/kg) | 10 | 0.39 ± 0.05*# |
| MCT + compound 1-1 of the present invention (50 mg/kg) | 10 | 0.34 ± 0.05# |
| MCT + 3-[(1-methyl-1H-indole-2-carbonyl)amino] propionic acid disclosed in CN2019107285315 (25 mg/kg) | 10 | 0.59 ± 0.07*# |
| MCT + sildenafil | 10 | 0.600 ± 06*# |

*means $P < 0.05$ compared with the normal control group, and
#means $P < 0.05$ compared with the MCT

Example 11: Effect of the Compounds of the Present Invention on the Survival Time of Animal Model of Sepsis A lipopolysaccharide (LPS)-induced mouse model of sepsis was used to determine the preventive and therapeutic effect of the compounds of the present invention (as exemplified by compounds 1-1 and 2-1 obtained in Examples 1 and 3) against sepsis. The method was as follows:

Experimental animals: 60 male C57BL/6J mice aged 6-8 weeks. The experimental animals were housed in an environment with room temperature of 25±2° C., 12 hours dark/12 hours light, and fed with conventional feed.

Survival analysis experiment: the mice were randomly divided into 6 groups of 10 mice each, namely, i) a solvent control group: each animal was administered 0.9% saline; ii) a sepsis model group (LPS group): each animal was injected intraperitoneally with LPS at a dose of 40 mg/kg; iii) a treatment group of medium-dose compound 1-1 (LPS+25 mg/kg of compound 1-1 obtained in Example 1): each animal was administered compound 1-1 by gavage at a dose of 25 mg/kg, followed by intraperitoneal injection of LPS at a dose of 40 mg/kg 30 minutes later; iv) a treatment group of high-dose compound 1-1 (LPS+50 mg/kg of compound 1-1 obtained in Example 1): each animal was administered compound 1-1 by gavage at a dose of 50 mg/kg, followed by intraperitoneal injection of LPS at a dose of 40 mg/kg 30 minutes later; v) a treatment group of high-dose compound 2-1 (LPS+50 mg/kg compound 2-1 obtained in Example 2): each animal was administered compound 2-1 by gavage at a dose of 50 mg/kg, followed by intraperitoneal injection of LPS at a dose of 40 mg/kg 30 minutes later; vi) a treatment group of medium-dose indole analogue 3-[(1-methyl-1H-indole-2-carbonyl)amino]propionic acid disclosed in CN2019107285315 (LPS+25 mg/kg of indole analogue 3-[(1-methyl-1H-indole-2-carbonyl)amino]propionic acid disclosed in CN2019107285315). The survival of the mice in each group was monitored, the time of death of the mice was recorded, and the average survival time of the animals in each group was calculated.

Results: the mice in the solvent control group survived for a long time; the mice in the LPS group began to die after about 12 hours, and the mortality rate of the mice reached more than 91% after about 20 hours. After a single injection of different doses of compound 1-1, the mice in the treatment groups of medium-dose compound 1-1 and high-dose compound 1-1 began to die after 20 hours and 28 hours, respectively, and after a single injection of the high-dose compound 2-1, the mice began to die after 22 hours. The average survival time of mice in the LPS group was 15.4±2.9 hours, the average survival time of mice in the treatment groups of medium-dose compound 1-1 and high-dose compound 1-1 was 24.8±3.9 hours and 26.4±4.3 hours, respectively and the average survival time of mice in the treatment group of high-dose compound 2-1 was 24.2±4.9 hours. The average survival time of mice in the treatment group of medium-dose indole analogue 3-[(1-methyl-1H-indole-2-carbonyl)amino]propionic acid disclosed in CN2019107285315 was 19.8±3.1 hours. Compared with the LPS group, the compounds of the present invention significantly prolonged the survival time of sepsis mice, and had a stronger therapeutic effect on sepsis than the indole analogue disclosed in CN2019107285315 at the same dose.

Example 12: Evaluation of the Effects of the Compounds of the Present Invention on Multiple Organ Damage in Sepsis A lipopolysaccharide (LPS)-induced mouse model of sepsis was used to determine the preventive and therapeutic effect of the compounds of the present invention (as exemplified by compound 1-1 obtained in Example 1) on cardiopulmonary injury caused by sepsis. The method was as follows:

Grouping of animals: 50 male C57BL/6J mice aged 6-8 weeks. The mice were randomly divided into 5 groups of 10 mice each, namely, i) a solvent control group: each animal was administered 0.9% saline; ii) a sepsis model group (LPS group): each animal was injected intraperitoneally with LPS at a dose of 40 mg/kg; iii) a treatment group of medium-dose compound 1-1 of Example (LPS+25 mg/kg of compound 1-1 obtained in Example 1): each animal was administered compound 1-1 by gavage at a dose of 25 mg/kg, followed by intraperitoneal injection of LPS at a dose of 40 mg/kg 30 minutes later; iv) a treatment group of high-dose compound 1-1 of Example 1 (LPS+50 mg/kg of compound 1-1 group obtained in Example 1): each animal was administered compound 1-1 by gavage at a dose of 50 mg/kg, followed by intraperitoneal injection of LPS at a dose of 40 mg/kg 30 minutes later; v) a treatment group of medium-dose indole analogue 3-[(1-methyl-1H-indole-2-carbonyl)amino]propionic acid disclosed in CN2019107285315 (LPS+25 mg/kg of indole analogue 3-[(1-methyl-1H-indole-2-carbonyl) amino]propionic acid disclosed in CN2019107285315): each animal was administered the indole analogue by gavage at a dose of 25 mg/kg, followed by intraperitoneal injection of LPS at a dose of 40 mg/kg 30 minutes later. 4 hours after LPS stimulation, follow-up examinations were performed in each group.

Assessment of cardiac function in mice: 4 animals from each group were used for this assay. Isoflurane was used to maintain proper anesthesia and spontaneous breathing in the mice. The mice were placed in the supine position on a constant temperature pad at 37° C., and the extremities of the mice were connected to four electrodes with conductive paste and fixed on the ultrasonic operating table. The probe was coated with ultrasound coupling agent, and placed in the lower middle part of the left sternum of the mice, and the short-axis M-mode echocardiographic images of the left ventricle adjacent to the sternum were acquired in real time. The dynamic images of 10 consecutive cardiac cycles were acquired using M-mode echocardiography, and the images were stored and analyzed offline. Left ventricular ejection fraction (LVEF) and left ventricular fraction shortening (LVFS) were calculated from left ventricular end diastolic diameter (LVEDD) and left ventricular end systolic diameter (LVESD), respectively, using the formulae: $LVEF=(LVEDD^3-LVESD^3)/LVEDD^3\times100\%$ and $LVFS=(LVEDD-LVESD)/LVEDD\times100\%$.

Determination of lung coefficient: after weighting, the mice were anesthetized with pentobarbital sodium injection, and the whole lung was removed from the thorax, and the tissue around the lung was removed. Surface moisture and blood stains were wiped dry with filter paper, and the wet weight of the lung was weighed. Lung coefficient=lung wet weight (mg)/mouse body weight (g)×100%.

Histopathological observations: after the mice were anaesthetized with pentobarbital sodium injection, the lungs and ventricles were removed by thoracotomy and fixed in 10% neutral formaldehyde (pH=7.4) for 2 days. Routine paraffin embedding, serial sectioning, H&E staining, neutral balsam sealing and microscopic observation were performed.

Results: LVEF and LVFS are the main indexes of cardiac systolic function. 4 hours after intraperitoneal injection of LPS, compared with the solvent control group, left ventricular systolic function of mice in the LPS model group was obviously altered, showing a significant decrease in contractility, and LVEF and LVFS were significantly lower than those in the control group, as shown in Table 3. Compared with the LPS group, left ventricular systolic function of mice was significantly improved in the treatment groups of medium-dose compound 1-1 and high-dose compound 1-1, the LVEF index was 58.7±4.3% and 63.8±3.9%, respectively, and the LVFS index was 24.5±2.6% and 30.7±2.2%, respectively. Compared with the LPS group, left ventricular systolic function of mice was significantly improved in the mice of the treatment group of medium-dose indole analogue 3-[(1-methyl-1H-indole-2-carbonyl)amino]propionic acid disclosed in CN2019107285315, the LVEF index was 53.2±3.8%; and the LVFS index was 22.9±4.0%. The above results show that the compounds of the present invention have significant ameliorative effects on LPS-induced cardiac dysfunction in mice, and their ameliorative effects on LPS-induced cardiac dysfunction in mice are stronger than those of the indole analogue disclosed in CN2019107285315 at the same dose.

TABLE 3

Effect of the compounds of the present invention on cardiac function in septic mice

| Parameters | Solvent control group | Model group | Treatment group of medium-dose compound 1-1 | Treatment group of high-dose compound 1-1 | Treatment group of medium-dose 3-[(1-methyl-1H-indole-2-carbonyl)amino]propionic acid disclosed in CN2019107285315 |
|---|---|---|---|---|---|
| LVEF (%) | 71.0 ± 4.9 | 34.3 ± 2.9* | 58.7 ± 4.3*# | 63.8 ± 3.9*# | 53.2 ± 3.8*# |
| LVFS (%) | 36.6 ± 2.5 | 15.2 ± 2.8* | 24.5 ± 2.6*# | 30.7 ± 2.2*# | 22.9 ± 4.0*# |

*means P < 0.05 compared with the solvent control group,
#means P < 0.05 compared with the model group Effect of the compounds of the present invention on lung coefficient: the lung coefficient is used to express the water content of the lung and to assess the degree of pulmonary edema. 4 hours after stimulation by intraperitoneal injection of LPS at 40 mg/kg, the lung coefficient of mice in the LPS model group was significantly increased, which was 7.24%±0.21% (P<0.05), compared with the solvent control group (4.21±0.29%); the lung coefficients of mice in the treatment groups of medium-dose compound 1-1 and high-dose compound 1-1 decreased compared with the LPS group, which were 5.16%±0.19% and 4.93%±0.12%, respectively. The treatment group of medium-dose indole analogue 3-[(1-methyl-1H-indole-2-carbonyl)amino]propionic acid disclosed in CN2019107285315 showed a reduced lung coefficient (5.48%±0.15%) in mice compared with the LPS group, and its therapeutic effect was significantly weaker than that of compound 1-1 of the present invention at the same dose.

The compounds of the present invention alleviated LPS-induced pathological damage to myocardial and lung tissue in mice: no inflammatory cell infiltration was seen in myocardial tissue of the mice in the solvent control group; lung tissue was structurally intact, with well-defined alveolar lumens and no inflammatory cell infiltration was seen. Myocardial tissue of the mice in the LPS group showed obvious interstitial cell proliferation and oedema, with inflammatory cell infiltration in the interstitium; lung tissue showed dilation of alveolar septa, structural destruction of alveolar walls, hemorrhage in some alveoli, and a large number of inflammatory cell infiltrations in the pulmonary mesenchyme. Upon administration of different doses of the compounds of the present invention or the indole analogues disclosed in CN2019107285315, respectively, the inflammatory damage in myocardial tissue of the model mice was ameliorated, and the lung tissue lesions were milder than that of the model group, and the hemorrhage in alveoli and inflammatory cell infiltration were reduced.

The above results show that the compounds of the present invention have very obvious ameliorative effects on LPS-induced cardiac and pulmonary dysfunction in mice, and the ameliorative effects on LPS-induced cardiac and pulmonary dysfunction in mice are stronger than those of the indole analogue disclosed in CN2019107285315.

Example 13: Evaluation of the Effect of the Compounds of Present the Invention in Mouse Model of Tumor The preventive and therapeutic effect of the compounds of the present invention (as exemplified by compound 1-1 obtained in Example 1) on tumor was determined using a mouse model of H22 liver subcutaneous transplanted tumor. The method was as follows:

Grouping of animals: 50 male ICR mice with 18-22 g were randomly divided into 5 groups of 10 mice in each group: a solvent control group; a cyclophosphamide (CTX) group (20 mg/kg, positive drug); a treatment group of medium-dose compound 1-1 (25 mg/kg); a treatment group of high-dose compound 1-1 (50 mg/kg); and a treatment group of medium-dose indole analogue 3-[(1-methyl-1H-indoL-2-carbonyl)amino]propanoic acid disclosed in CN2019107285315 (25 mg/kg).

Experimental procedure: H22 hepatoma cell suspension was adjusted to $1\times10^7$/mL after dilution and counting with normal saline, and 0.2 mL per mouse was inoculated on the back of the mice. After 24 hours, the mice were weighed and administered drug at a dose of 0.1 mL/10 g once a day, wherein the mice in the solvent control group and the treatment groups were administered 0.9% sodium chloride solution and the compound of the present invention, respectively, for 14 days, and the mice in the CTX group were injected intraperitoneally for 14 days. The mice were weighed after 14 days. The animals were executed and the tumor blocks were removed and weighed separately. The tumor inhibition rate was calculated according to the following formula: tumor inhibition rate (%)=(1−average tumor weight in a treatment group/average tumor weight in the solvent control group)×100%.

Results: the tumor inhibition rate of the positive control CTX group was 60.3%; the tumor inhibition rates of the treatment groups of medium-dos compound 1-1 obtained in Example 1 obtained in Example 1 and high-dose compound 1-1 were 60.5% and 69.4%, respectively; and the tumor inhibition rate of the treatment group of medium-dose indole analogue 3-[(1-methyl-1H-indole-2-carbonyl)amino]propionic acid disclosed in CN2019107285315 was 52.8%. It shows that the compounds of the present invention have a significant inhibitory effect on the growth of H22 liver subcutaneous transplanted tumor, and the inhibitory effect on the growth of H22 liver subcutaneous transplanted tumor is stronger than that of the indole analogue disclosed in CN2019107285315.

Example 14: Therapeutic Effect of the Compounds of the Present Invention on Renal Fibrosis The therapeutic effect of the compounds of the present invention (as exemplified by Compound 1-1 obtained in Example 1) on renal fibrosis was determined using a mouse model of renal fibrosis. The method was as follows:

Grouping of animals: male C57BL/6J mice aged 8 weeks were given adaptive feeding for 3 days and grouped into a sham operation group, a sham operation-treatment group, a Unilateral ureteral obstruction (UUO) model group, a low-dose (10 mg/kg) treatment group, a medium-dose (25 mg/kg) treatment group, a high-dose (50 mg/kg) treatment group, a medium-dose (25 mg/kg) treatment group of indole analogue 3-[(1-methyl-1H-indole-2-carbonyl)amino]propionic acid disclosed in CN2019107285315, and a positive control group of losartan (50 mg/kg), with 10 animals in each group. Mice in the model and the treatment groups were anesthetized by intraperitoneal injection of 0.5% sodium pentobarbital at a dose of 0.1 mL/10 g. The mice were fixed on the operating table and cut open in layers from the right side of the mid-abdomen to locate the left kidney, and the ends of the ureter were ligated, while the ureter was cut off between the two ligations; the sham operation group was operated as described above and the ligations were not performed. Post-operative organs were repositioned, sutured, and sterilized with iodophor after suturing was completed. Immediately after operation, the drug was administered by gavage once daily for 14 days. Urine sample collection: animals were placed in separate metabolic cages by group on days 0, 5, 10 and 14 after modelling, without food or water, and urine samples were collected from each group of mice.

The protein levels in urine were determined using Coomassie brilliant blue (CBB) method by using urine protein quantitative test kit (Nanjing Jiancheng Bioengineering Institute). CBB working solution was prepared according to the kit instructions. 0.05 mL of each urine sample was mixed with 3 mL of CBB working solution, the mixture was left to stand for 5 min, and the absorbance value of each sample was determined at 595 nm. The protein levels in each group of urine samples were calculated according to the protein standardization formula: urine protein levels (mg/L) =(measured OD−blank OD)/(standard OD−blank OD)×563 mg/L.

Collection of serum sample: orbital blood from each mouse was collected in an EP tube, placed at 37° C. for 20 minutes, and centrifuged to obtain the upper layer of serum.

Collection of plasma sample: orbital blood from each mouse was collected in an anticoagulation tube, mixed well and stored at 4° C. for later use.

Determination of creatinine levels in urine and serum by the picric acid colorimetric method: creatinine levels in urine and serum were determined by using the creatinine test kit (Nanjing Jiancheng Bioengineering Institute). According to the kit instructions, 1.5 mL of urine sample or serum sample and 0.5 mL of picric acid solution, 0.5 mL of 0.5 mol/L sodium hydroxide solution were mixed, heated in water bath at 37° C. for 10 minutes. The absorbance value of each sample was determined using a UV spectrophotometer at a wavelength of 510 nm. Creatinine levels in samples of each group were calculated according to the formula: creatinine level (μmol/L) in serum or urine=(measured OD value−blank OD value)/(standard OD value−blank OD value)×50 μmol/L×(dilution ratio 201).

Determination of urea nitrogen level in plasma by diacetyl monoxime method: urea nitrogen level was determined was determined by using blood urea nitrogen (BUN) test kit (Nanjing Jiancheng Bioengineering Institute). According to the kit instructions, 0.05 mL of anticoagulated plasma samples were mixed with 1 mL of oxime solution and 1 mL of acid working solution, and the mixtures were placed in a boiling water bath for 15 min. A UV-visible spectrophotometer was used to determine the absorbance values of each tube at a wavelength of 520 nm. Urea nitrogen levels in plasma samples of each group were calculated according to the formula: Urea nitrogen level (mmol/L)=(measured OD value−blank OD value)/(standard OD value−blank OD value)×10 mmol/L.

Collection of kidney tissue samples: kidneys were taken from mice after anesthesia, cut horizontally, and the upper part of the kidneys was embedded in OCT embedding box, sliced with frozen slicer and stored at −20° C.

H&E staining was used to evaluate pathological glomerular changes, and the procedure was as follows: frozen sections were fixed with 95% ethanol for 2 min, hydrated with distilled water, stained with hematoxylin for 3 minutes, washed with distilled water for 3 min, differentiated using 1% hydrochloric acid in ethanol for 10 s, washed with distilled water for 30 seconds, returned to blue in running water for 5 min, washed in distilled water for 30 s, stained with eosin for 30 seconds, washed with 75% and 85% ethanol for 20 seconds each, dehydrated rapidly with 95% ethanol for 1 min, dehydrated with anhydrous ethanol, cleared to transparency in xylene (1 min×3), and finally sealed with neutral balsam and photographed with a biomicroscope.

Data statistics and analysis: SPSS22.0 software was used for data analysis, all data were expressed as mean±standard error (mean±SEM), two-sample t-test was used to compare means between two groups; one-way ANOVA was used to compare means between multiple groups, and Turkey's method was used to compare two groups. A significance level of P<0.05 indicates a statistically significant difference between groups.

Results: body weights and kidney weights of mice in each group were weighed after modelling. Compared with the sham operation group, the body weight of the mice in the model group decreased by 18.5% (20.2±1.1 g vs. 24.8±0.7 g, P<0.01) and the kidney weight increased by 62.5% (0.26±0.02 g vs. 0.16±0.01 g, P<0.01). Compared with the UUO model group, there was a slight increase in body weight and a slight decrease in kidney weight of the mice in the low-dose treatment group of compound 1-1, the medium-dose treatment group of compound 1-1, the high-dose treatment group of compound 1-1, the medium-dose treatment group of indole analogue 3-[(1-methyl-1H-indole-2-carbonyl)amino]propionic acid disclosed in CN2019107285315 and the positive control group of losartan, but none of them were statistically different (P>0.05). The above results show that the drug does not affect the body weight and kidney weight of the UUO model mice.

Compared with the sham operation group, urine protein level, serum urea nitrogen levels and creatinine level of the mice in the model group were increased by 465.6%, 79.4% and 48.7%, respectively (urine protein level: 888.5±264.8 mg/mL vs. 157.1±13.46 mg/mL, P<0.01; serum urea nitrogen level: 17.56±0.48 mmol/L vs. 9.79±0.60 mmol/L, P<0.001; serum creatinine level: 32.48±0.87 μmol/L vs. 21.84±0.91 μmol/L, P<0.001). Compared with the model group, urinary protein level, urea nitrogen level and creatinine level of the mice in the low-dose treatment group of compound 1-1, the medium-dose treatment group of compound 1-1, the high-dose treatment group of compound 1-1 were significantly reduced in a dose-dependent manner. Among them, in the low-dose treatment group of compound 1-1 at a dose of 10 mg/kg, urine protein level was reduced by 27.4% (645.2±164.6 mg/mL vs. 888.5±264.8 mg/mL, P<0.05), urea nitrogen level and creatinine level was reduced by 24.7% (13.23±0.62 mmol/L vs. 17.56±0.48 mmol/L, P<0.001) and 17.2% (26.88±0.86 μmol/L vs. 32.48±0.87 μmol/L, P<0.001), respectively. In the medium-dose treatment group of compound 1-1 at a dose of 25 mg/kg, urine protein level was reduced by 37.7% (553.5±142.9 mg/mL vs. 888.5±264.8 mg/mL, P<0.01), and urea nitrogen level and creatinine level were reduced by 30.0% (12.30±0.33 mmol/L vs. 17.56±0.48 mmol/L, P<0.001) and 20.7% (25.76±1.31 μmol/L vs. 32.48±0.87 μmol/L, P<0.001). In the high-dose treatment group of compound 1-1 at a dose of 50 mg/kg, urine protein level was reduced by 52.6% (421.4±82.26 mg/mL vs. 888.5±264.8 mg/mL, P<0.01), and urea nitrogen level and creatinine level were respectively reduced by 37.7% (10.94±0.42 mmol/L vs. 17.56±0.48 mmol/L, P<0.001) and 27.6% (23.52±0.86 μmol/L vs. 32.48±0.87 μmol/L, P<0.001), respectively. In the medium-dose treatment group of indole analogue 3-[(1-methyl-1H-indole-2-carbonyl)amino]propionic acid disclosed in CN2019107285315, urine protein level was reduced by 30.1% (621.3±81.33 mg/mL vs. 888.5±264.8 mg/mL, P<0.01), urea nitrogen level and creatinine level were reduced by 20.6% (13.94±0.42 mmol/L vs. 17.56±0.48 mmol/L, P<0.001) and 18.3% (26.52±0.86 μmol/L vs. 32.48±0.87 μmol/L, P<0.001), respectively. In the positive control group of losartan, urine protein level was reduced by 46.6% (474.9±112.5 mg/mL vs. 888.5±264.8 mg/mL, P<0.01), urea nitrogen level and creatinine level were reduced by 29.7% (12.35±0.37 mmol/L vs. 17.56±0.48 mmol/L, P<0.001) and 19.0% (26.32±1.12 μmol/L vs. 32.48±0.87 μmol/L, P<0.001), respectively. Thus, compound 1-1 of the present invention has significant ameliorative effects on UUO-induced renal fibrosis in a mouse model, and the ameliorative effect of compound 1-1 on renal fibrosis is significantly stronger than those of the indole analogue 3-[(1-methyl-1H-indole-2-carbonyl)amino]propionic acid disclosed in CN2019107285315 at the same dose.

Figure 2:
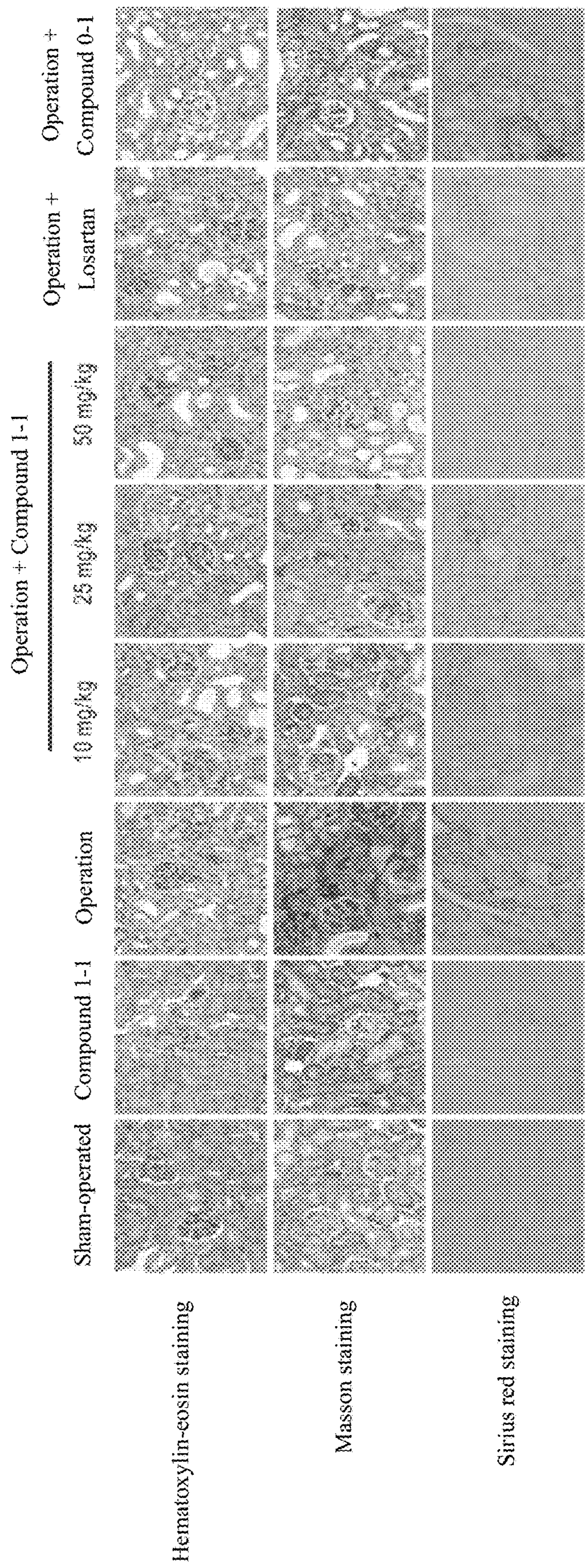
FIG. 2 shows renal fibrotic renal tissues after treatment with compound 1-1 of the present invention, which are stained with hematoxylin-eosin staining, Masson staining and Sirius red staining, respectively. Note: Compound 0-1 is 3-[(1-methyl-1H-indole-2-carbonyl)amino]propionic acid, which is the most active indole analogue disclosed in CN2019107285315.

To investigate the effect of compound 1-1 on renal injury in the mouse model of UUO, the extent of renal fibrosis in each group was examined using pathological staining. The results of H&E, Masson and Sirius red staining (FIG. 2) show that significant renal tubular lumen dilatation, glomerular atrophy, interstitial occurrence of inflammatory cell infiltration, and a large amount of fibrotic tissue proliferation are observed in mice of the UUO model group, compared with the sham operation group; compound 1-1 significantly attenuates tubular lumen dilatation and glomerular atrophy in a dose-dependent manner, reduces the occurrence of inflammatory cell infiltration and fibrous tissue proliferation in the interstitium, and increases epithelial cell integrity; losartan shows the same effect; however, compared with compound 1-1, the indole analogue 3-[(1-methyl-1H-indole-2-carbonyl)amino]propionic acid disclosed in CN2019107285315 shows less improvement in fibrotic tissue proliferation and renal tubular lumen dilation at the same dose. The above results clearly show that the compounds of the present invention significantly ameliorate UUO-induced renal fibrosis, and that this therapeutic effect is significantly stronger than that of the indole analogue disclosed in CN2019107285315.

The foregoing is merely a preferred embodiment of the present invention and is not intended to limit the present invention, which will be subject to various changes and variations to those skilled in the art. Any modifications, equivalent substitutions, improvements, etc. made within the spirit and principles of the present invention shall be included in the scope of protection of the present invention.

The invention claimed is:

1. An indole carboxamide compound represented by formula (I) or pharmaceutically acceptable salts thereof:

(I)

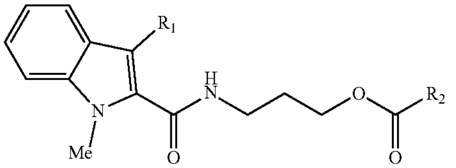

wherein:

$R_1$ is selected from a group consisting of hydrogen atom, hydroxyl, aldehyde group, halogen, guanidino, $C_{1-6}$ alkyl, $C_{2-6}$ alkenyl, $C_{2-6}$ alkynyl, 6- to 14-membered aryl, 5- to 6-membered heteroaryl, $C_{1-6}$ alkyloxy, 6- to 14-membered aryloxy, —$OCH_2$-6- to 14-membered aryl, —$CF_3$, —$OCHF_2$, —$OCF_3$, —CN, nitro group, carboxyl, —C(O)O—$C_{1-6}$ alkyl, —C(O)N—$C_{1-6}$ alkyl, amino group, —NHC(O)—$C_{1-6}$ alkyl, —S—$C_{1-6}$ alkyl, —SO—$C_{1-6}$ alkyl, —$SO_2$-$C_{1-6}$ alkyl or a heterocyclic ring containing 1~4 heteroatoms selected from N, O and S; the $C_{1-6}$ alkyl, the 6- to 14-membered aryl or the 5- to 6-membered heteroaryl are optionally substituted with 1 to 5 substituents selected from a group consisting of hydroxyl, nitro group, sulfonic group, halogen, cyano, trifluoromethyl, difluoromethoxy or trifluoromethoxy; and the 5- to 6-membered heteroaryl optionally contain 1 to 6 heteroatoms selected N, O and S;

$R_2$ is selected from a group consisting of hydrogen atom, $C_{1-10}$ alkyl, 6- to 14-membered aryl, 5- to 6-membered heteroaryl, amino group, substituted amino group, amidino group or guanidino; wherein the $C_{1-10}$ alkyl, the 6- to 14-membered aryl or the 5- to 6-membered heteroaryl are optionally substituted with 1 to 2 substituents selected from a group consisting of hydroxyl, nitro group, halogen, cyano, trifluoromethyl, 6- to 8-membered aryl, trifluoromethoxy or difluoromethoxy; and the 5- to 6-membered heteroaryl optionally contain 1 to 6 heteroatoms selected from N, O and S.

2. The indole carboxamide compound represented by formula (I) or pharmaceutically acceptable salts thereof according to claim 1, wherein in the formula (I):

$R_1$ is selected from a group consisting of hydrogen atom, hydroxyl, aldehyde group, halogen, 6- to 14-membered aryl group, —CN, amino group or nitro group;

$R_2$ is selected from a group consisting of hydrogen atom, $C_{1-6}$ alkyl or phenyl.

3. The indole carboxamide compound represented by formula (I) or pharmaceutically acceptable salts thereof according to claim 1, wherein the indole carboxamide compound is selected from the following compounds or pharmaceutically acceptable salts thereof:

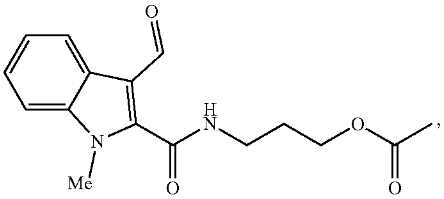,

-continued

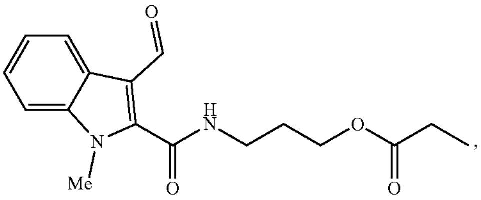,

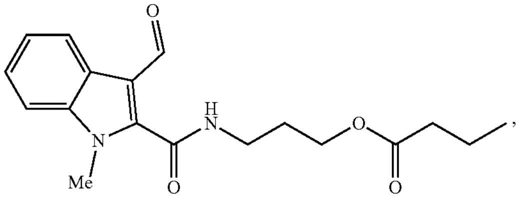,

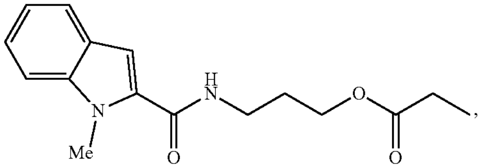,

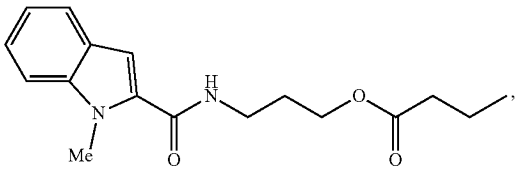,

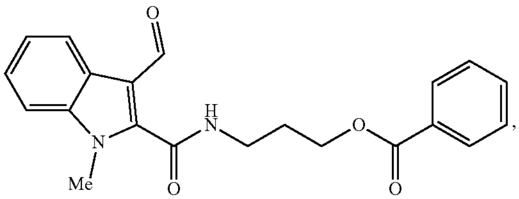,

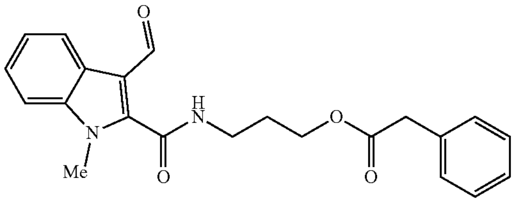 or

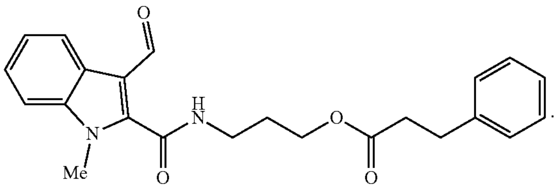.

4. A method for preparing the indole carboxamide compound represented by formula (I) or pharmaceutically acceptable salts thereof according to claim 1, which is either one of the following two methods:

method 1

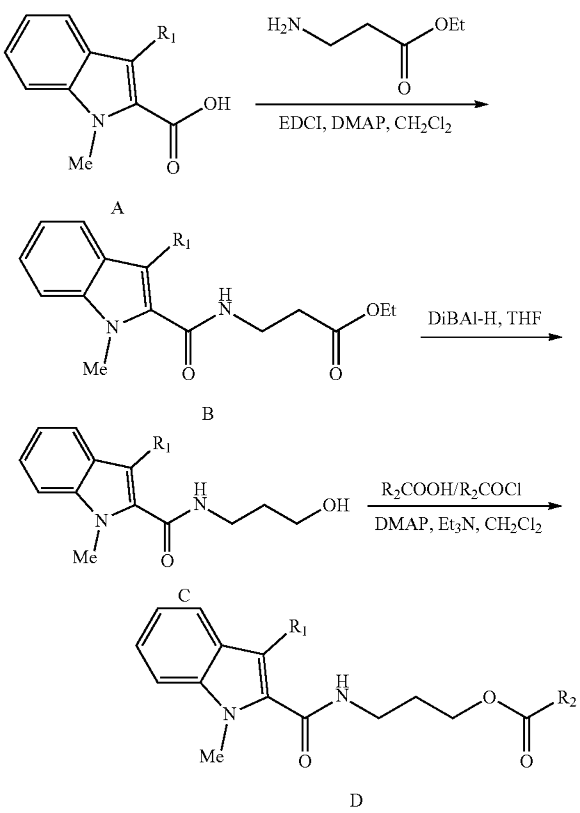

wherein, $R_1$ and $R_2$ are defined as in claim 1;

compound A is dissolved in anhydrous dichloromethane ($CH_2Cl_2$), 1-(3-dimethylaminopropyl)-3-ethylcarbodiimide hydrochloride (EDCI) is dissolved in anhydrous $CH_2Cl_2$, and β-alanine ethyl ester and 4-dimethylaminopyridine (DMAP) are dissolved in anhydrous $CH_2Cl_2$, and then the three solutions are mixed to react under stirring in an ice bath, and then reacted at room temperature, and the reaction is monitored by TLC until it is complete;

then the reaction is quenched by adding saturated ammonium chloride ($NH_4Cl$) solution drop by drop and thus obtained mixture is extracted with $CH_2Cl_2$, lower layer solution is collected, dried with anhydrous sodium sulfate ($Na_2SO_4$), filtered, concentrated, and purified by column chromatography to give product B;

the product B obtained above is dissolved in anhydrous tetrahydrofuran (THF) under stirring, following by adding diisobutylaluminum hydride (DIBAl-H) drop by drop, the reaction is carried out at 0° C. and monitored by TLC until it is complete; then methanol (MeOH) is added drop by drop to quench the reaction, and a small amount of methyl tertiary-butyl ether (MTBE) is added to dilute reaction system, and saturated sodium potassium tartrate solution is added to further quench reaction, and stirring is continued until the reaction system is clarified; after clarification, reaction system is extracted with ethyl acetate (EtOAc), organic phases are combined, washed with a small amount of saturated brine, and then organic phases are dried with anhydrous $Na_2SO_4$, and then concentrated after a few moments of standing, and then purified by column chromatography to give product C;

the product C obtained above is dissolved in anhydrous $CH_2Cl_2$ under stirring, followed by successively adding triethylamine ($Et_3N$) and DMAP at room temperature, and finally compound $R_2COOH$ or its anhydride, or its acyl chloride $R_2COCl$ is added drop by drop to initiate reaction; reaction is monitored by TLC until it is complete; saturated $NH_4Cl$ solution is added drop by drop to quench reaction, thus obtained mixture is extracted with ethyl acetate, organic phases are combined, washed with a small amount of saturated brine, dried with anhydrous $Na_2SO_4$, filtered, concentrated, and purified by column chromatography to give product D;

method 2

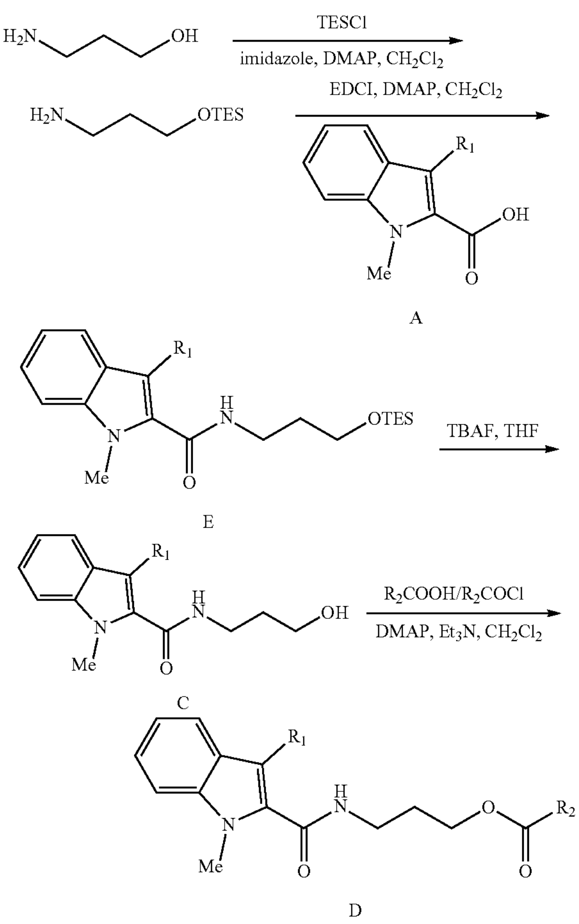

wherein, $R_1$ and $R_2$ are defined as in claim 1;

3-aminopropanol is dissolved in anhydrous $CH_2Cl_2$, followed by adding imidazole and 4-dimethylaminopyridine (DMAP), and finally triethylchlorosilane (TESCl) is added under stirring at room temperature, and reaction is monitored by TLC until it is complete; saturated $NH_4Cl$ solution is added drop by drop to quench reaction, and then thus obtained is extracted with ethyl acetate, organic phases are combined, washed with a small amount of saturated brine, and then dried with anhydrous $Na_2SO_4$, filtered, concentrated, and purified by column chromatography to give 3-triethylsilyloxy-1-propanamine;

the compound A is dissolved in anhydrous $CH_2Cl_2$, 1-(3-dimethylaminopropyl)-3-ethylcarbodiimide hydrochloride (EDCI) is dissolved in anhydrous $CH_2Cl_2$, 3-triethylsilyloxy-1-propanamine and DMAP are dissolved in anhydrous $CH_2Cl_2$, and then the above three solutions are mixed, and thus obtained mixture is stirred in an ice bath and then reacted at room temperature, and reaction is monitored by TLC until it is complete; thus obtained mixture is extracted with $CH_2Cl_2$, and lower layer solution is collected and dried overnight with anhydrous $Na_2SO_4$, then filtered and concentrated, and purified by column chromatography to give product E;

the compound E is dissolved in anhydrous tetrahydrofuran (THF), followed by adding a small amount of tetrabutylammonium fluoride (TBAF) under stirring at room temperature and reaction is monitored by TLC until it is complete; the reaction is quenched by adding saturated $NH_4Cl$ solution drop by drop, thus obtained mixture is extracted with EtOAc, and organic phases are combined, washed with a small amount of saturated brine, dried with anhydrous $Na_2SO_4$, filtered, concentrated, and purified by column chromatography to give product C;

the product C obtained above is dissolved in anhydrous $CH_2Cl_2$ under stirring, followed by successively adding triethylamine ($Et_3N$) and DMAP at room temperature, and finally compound $R_2COOH$ or its anhydride, or its acyl chloride $R_2COCl$ is added drop by drop to initiate reaction; the reaction is monitored by TLC until it is complete; saturated $NH_4Cl$ solution is added drop by drop to quench the reaction, thus obtained mixture is extracted with EtOAc, organic phases are combined, washed with a small amount of saturated brine, dried with anhydrous $Na_2SO_4$, filtered, concentrated, and purified by column chromatography to give product D.

5. A method of inhibiting transient receptor potential canonical channel 6 (TRPC6) in a subject in need thereof, comprising administering to the subject an effective amount of the indole carboxamide compound represented by formula (I) or pharmaceutically acceptable salts thereof according to claim 1.

6. A method of inhibiting transient receptor potential canonical channel 6 (TRPC6) channel-mediated $Ca^{2+}$ entry in a subject in need thereof, comprising administering to the subject an effective amount of the indole carboxamide compound represented by formula (I) or pharmaceutically acceptable salts thereof according to claim 1.

7. A method of treating a disease selected from the group consisting of nephropathy, sepsis, arthritis, pulmonary hypertension and tumor in a subject in need thereof, comprising administering to the subject an effective amount of the indole carboxamide compound represented by formula (I) or pharmaceutically acceptable salts thereof according to claim 1.

8. The method Use-according to claim 7, wherein the nephropathy is a primary glomerular disease, including primary nephrotic syndrome, IgA nephropathy, acute glomerulonephritis, focal segmental glomerulosclerosis, renal fibrosis, idiopathic membranous nephropathy, and membranoproliferative glomerulonephritis; metabolic disease-associated renal damage, including diabetic nephropathy, hyperuricemic nephropathy and obesity-related glomerulopathy; chronic renal failure, including cardiovascular complications due to renal anemia and chronic renal failure; and infection-related renal damage, including hepatitis B virus-related nephritis, and renal lesion due to infective endocarditis;

the sepsis comprises sepsis and septic shock caused by a variety of different pathogenic bacteria, including, but not limited to: *Staphylococcus aureus* septicemia, septicemia caused by *Staphylococcus epidermidis, Enterococcal septicemia*, gram-negative *Bacillus* septicemia, anaerobic bacteria septicemia, fungal septicemia and septic shock;

the pulmonary hypertension comprises, but is not limited to, pulmonary arterial hypertension, pulmonary hypertension caused by left heart disease, pulmonary hypertension caused by hypoxia and/or lung disease, chronic thromboembolic pulmonary hypertension, pulmonary hypertension due to multiple mechanisms and/or unknown mechanisms;

the tumor comprises a malignant tumor; the malignant tumor comprises, but is not limited to: glioma, esophageal cancer, renal cancer, pancreatic cancer, breast cancer, lung cancer, liver cancer and colorectal cancer.

9. A pharmaceutical composition comprising the indole carboxamide compound represented by formula (I) or pharmaceutically acceptable salts thereof according to claim 1 and a pharmaceutically acceptable excipient.

10. The indole carboxamide compound represented by formula (I) or pharmaceutically acceptable salts thereof according to claim 1, wherein in the formula (I):

$R_1$ is selected from a group consisting of hydrogen atom, aldehyde group, amino group and phenyl;

$R_2$ is selected from a group consisting of $C_{1-3}$ alkyl and phenyl.

11. The indole carboxamide compound represented by formula (I) or pharmaceutically acceptable salts thereof according to claim 1, wherein the indole carboxamide compound is selected from the following compounds or pharmaceutically acceptable salts thereof:

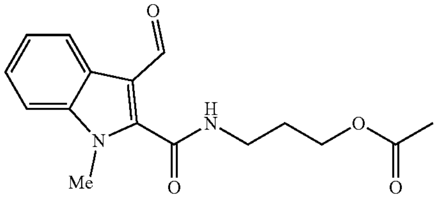

and

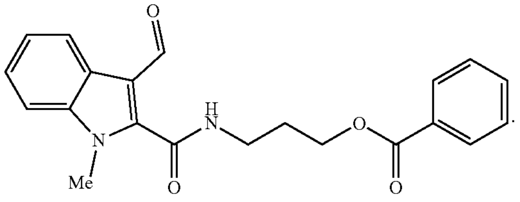

12. The indole carboxamide compound represented by formula (I) or pharmaceutically acceptable salts thereof according to claim 1, wherein the indole carboxamide compound is selected from a group consisting of the following compound and pharmaceutically acceptable salts thereof:

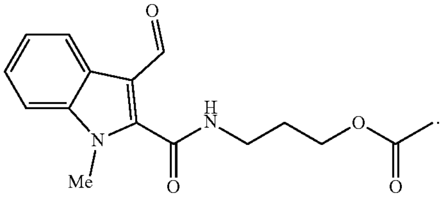 [SMILES: CC(=O)OCCCNC(=O)c1c(C=O)c2ccccc2n1C]

* * * * *